United States Patent
Ericsson et al.

(10) Patent No.: US 6,825,233 B2
(45) Date of Patent: Nov. 30, 2004

(54) COMPOUNDS HAVING RETINOID-LIKE ACTIVITY

(75) Inventors: Anna Ericsson, Shrewsbury, MA (US); Anne Marinier, Kirkland (CA); Fred C. Zusi, Hamden, CT (US)

(73) Assignee: Bristol-Myers Squibb Company, Princeton, NJ (US)

(*) Notice: Subject to any disclaimer, the term of this patent is extended or adjusted under 35 U.S.C. 154(b) by 3 days.

(21) Appl. No.: 10/075,845

(22) Filed: Feb. 13, 2002

(65) Prior Publication Data

US 2002/0193421 A1 Dec. 19, 2002

Related U.S. Application Data

(60) Provisional application No. 60/269,473, filed on Feb. 16, 2001.

(51) Int. Cl.⁷ ................ A61K 31/235; A61K 31/19; C07C 69/76; C07C 65/24
(52) U.S. Cl. ................ 514/544; 514/569; 560/56; 562/466
(58) Field of Search ................ 514/544, 569, 514/437, 469; 560/56; 562/466; 549/26

(56) References Cited

U.S. PATENT DOCUMENTS

| 5,075,487 A |   | 12/1991 | Akasaki et al. |
| 5,618,839 A | * | 4/1997 | Starrett, Jr. et al. |

FOREIGN PATENT DOCUMENTS

| EP | 0708100 | 4/1996 |
| EP | 0709382 | 5/1996 |

OTHER PUBLICATIONS

Roberts et al., the Retinoids, Academic Press, New York pp209–286 (1984).
Lippman et al., Cancer Treat Rep. 71:391–405 (1987).
Hong et al., N. Engl. J. Med. 323:795–801 (1990).
Huang et al., Blood 72:567–572 (1988).
Loeliger et al., Eur. J. Med. Chem. 15:9–15 (1980).
Kagechika et al., J. Med. Chem. 31(11):2182–2192 (1988).
Coffey et al., Retinoids as Potential Antirheumatic Agents, Chemistry and Biology of Synthetic Retinoids, CRC Press Inc. pp520–537 (1990).
Orfanos et al., Drugs 34:459–503 (1987).
Lippman et al., Cancer Treat Rep. 71:483–515 (1987).

* cited by examiner

*Primary Examiner*—Johann Richter
*Assistant Examiner*—Paul A. Zucker
(74) *Attorney, Agent, or Firm*—Maureen S. Gibbons

(57) ABSTRACT

There are provided compounds represented by the formula I

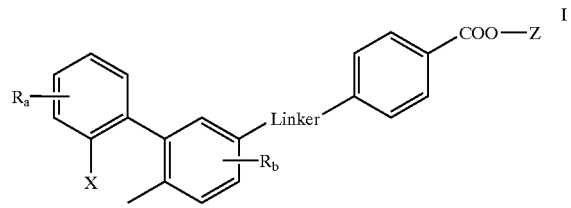

or a nontoxic pharmaceutically acceptable salt, physiologically hydrolyzable ester or solvate thereof, wherein the various substituents are as defined. Also included are methods for preventing and/or treating tumors, arthritis, and non-malignant skin disorders comprising administering a compound of formula I to a mammal. Further provided are pharmaceutical formulations comprising a compound of formula I in admixture with one or more pharmaceutically acceptable excipients.

7 Claims, No Drawings

COMPOUNDS HAVING RETINOID-LIKE ACTIVITY

RELATED APPLICATIONS

This application claims the benefit under 35 U.S.C. Section 119(e) of U.S. Provisional Patent Application No. 60/269,473, filed Feb. 16, 2001.

FIELD OF THE INVENTION

The present invention provides compounds having retinoid-like activity. More specifically, the compounds of the present invention are useful for preventing and/or treating various skin disorders, such as, but not limited to, acne, psoriasis and damage from irradiation. Further, they have antitumor and antiarthritic activities.

BACKGROUND

Retinoic acid and its natural and synthetic analogues (retinoids) exert a wide array of biological effects.

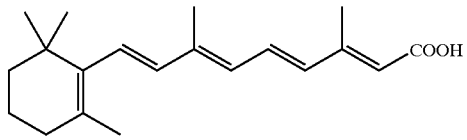

Retinoic Acid

They have been shown to affect cellular growth and differentiation and are promising drugs for the treatment of several cancers. See, for example, Roberts, A. B. and Sporn, M. B. in "The Retinoids," Sporn, et al. eds, 1984, 2, pp. 209–286, Academic Press, New York; Lippman, et al., Cancer Treat. Rep., 1987, 71, p. 391; ibid., p. 493; Hong et al., N. Engl. J. Med., 1990, 323, p. 795; Huang, M. et al., Blood, 1988, 72, p. 567.

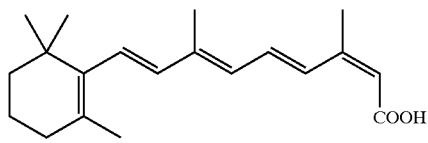

Retinoids have also been shown to be useful in treating rheumatic diseases. See, e.g. Coffey et al., Retinoids as Potential Antirheumatic Agents, Chemistry and Biology of Synthetic Retinoids, pp 520–537, CRC Press Inc., M. I. Dawson and W. H. Okamura Ed.(1990).

A few retinoids are already in clinical use in the treatment of dermatological diseases such as acne and psoriasis. For example, isotretinoin is used clinically for oral therapy of severe acne, and etretinate is particularly useful in the treatment of psoriasis. See, e.g., Orfanos et al., Drugs, 1987, 34, pp.459–503.

Isotretinoin

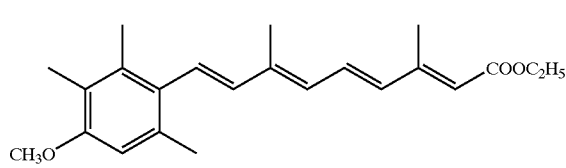

Etretinate

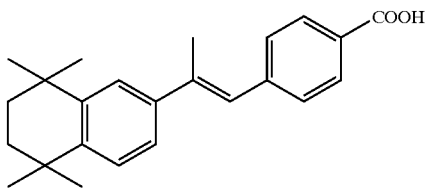

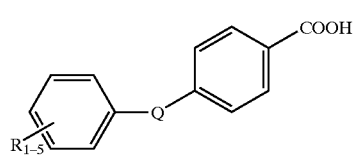

Other examples of retinoid compounds include arotinoid (formula II) and retinobenzoic acid (formula III), wherein Q equals —NHCO—, —CONH—, —COCH=CH—, —CH=CHCO—, —COCH$_2$—, and the like. See, e.g. Loeliger, et al. Eur. J. Med. Chem. 1980, 15, pp. 9–15; Kagechika, H. et al., J. Med. Chem., 1988, 31, No. 11, pp. 2182–2192.

Other compounds that have been reported include:

1. European 708,100 (Apr. 24, 1996), to C.I.R.D., covering the following structure:

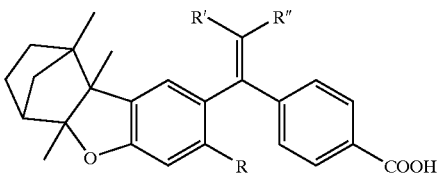

wherein R, R' and R" are as defined therein.

2. European 709,382 (May 1, 1996), to C.I.R.D, covering the following structure:

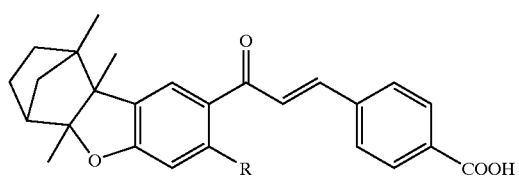

wherein R is as defined therein.

The compounds of the instant invention are distinguished from those above by the presence of a 2-atom "linker" joining the two phenyl rings, in contrast to the 1-atom or 3-atom linkers shown, and by the difference in the tricyclic rings. The compounds of the instant invention contain a tricyclic fused ring system with two optionally substituted aromatic rings, rather than the tetracyclic tetrahydromethanodibenzofuran fused ring system in the compounds shown above.

SUMMARY OF THE INVENTION

The present invention is directed to a compound having formula I:

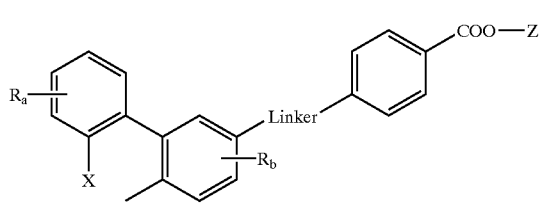

or a nontoxic pharmaceutically acceptable salt, physiologically hydrolyzable ester or solvate thereof, wherein $R_a$ and $R_b$ are independently selected from the group consisting of hydrogen, halogen, hydroxy, nitro, amino, substituted amino, mercapto, polyfluoroalkyl, $C_{1-6}$ alkyl, substituted $C_{1-6}$ alkyl, $C_{1-6}$ alkoxy, $C_{1-6}$ alkylthio, formyl, carboxyl, aryl or heteroaryl;

Linker is selected from the group consisting of $C_2$ alkyl, $C_2$ alkenyl, $C_2$ alkynyl, —C(=O)—NH—, —NH—C(=O)—, —CH$_2$O—, —O—C(=O)—, —C(=S)—NH—, —C(=O)—O—, —C(=O)—S—, —S—C(=O)—, —S—CH$_2$—, —CH$_2$—NH—, —C(=O)—CH$_2$—, —NH—C(=S)—, —CH$_2$S—, —OCH$_2$—, —NHCH$_2$;

X is O, S, —C(R$_1$)$_2$—, C=O, —C(R$_1$)$_2$Y— or —YC(R$_1$)$_2$—, wherein Y is selected from the group consisting of O, S and C(R$_2$)$_2$, wherein $R_1$ and $R_2$ are, independently, hydrogen or methyl; and Z is hydrogen or $C_{1-6}$ alkyl.

In some embodiments, $R_a$ and $R_b$ are independently selected from the group consisting of hydrogen, halogen, hydroxy, nitro, amino, mercapto, CF$_3$, $C_{1-6}$ alkyl, halosubstituted $C_{1-6}$ alkyl, hydroxy-substituted $C_{1-6}$ alkyl, aminosubstituted $C_{1-6}$ alkyl, $C_{1-6}$ alkoxy, $C_{1-6}$ alkylthio, formyl, carboxyl, mono- or di-$C_{1-6}$ alkyl-substituted amino, aryl or heteroaryl;

Linker is selected from the group consisting of —CH=CH—, —C≡C—, —C(=O)—NH—, —NH—C(=O)—, —CH$_2$O—, —O—C(=O)—, —C(=S)—NH—, —C(=O)—O—, —C(=O)—S—, —S—C(=O)—, —S—CH$_2$—, —CH$_2$—CH$_2$—, —CH$_2$—NH—, —C(=O)—CH$_2$—, —NH—C(=S)—, —CH$_2$S—, —OCH$_2$—, —NHCH$_2$ or —CRc=CRd-, wherein Rc and Rd are independently hydrogen or $C_{1-6}$ alkyl;

X is O, S, —C(R$_1$)$_2$—, C=O, —C(R$_1$)$_2$Y— or —YC(R$_1$)$_2$—, wherein Y is selected from the group consisting of O, S and C(R$_2$)$_2$ and $R_1$ and $R_2$ are, independently hydrogen or methyl; and Z is hydrogen or $C_{1-6}$ alkyl.

In some embodiments, X is —C(R$_1$)$_2$Y— or —YC(R$_1$)$_2$—, wherein Y is selected from the group consisting of O, S and C(R$_2$)$_2$ and $R_1$ and $R_2$ are, independently, hydrogen or methyl; and Z is hydrogen or $C_{1-6}$ alkyl.

In some embodiments, X is represented by O, S, C(R$_1$)$_2$, or C=O, wherein $R_1$ is hydrogen or methyl, resulting in a five-membered ring.

In some embodiments, the present invention is directed to pharmaceutical compositions comprising a therapeutically effective amount of the compounds of formula I and a pharmaceutically acceptable carrier therefor.

DETAILED DESCRIPTION OF THE INVENTION

The present invention relates to compounds represented by formula I

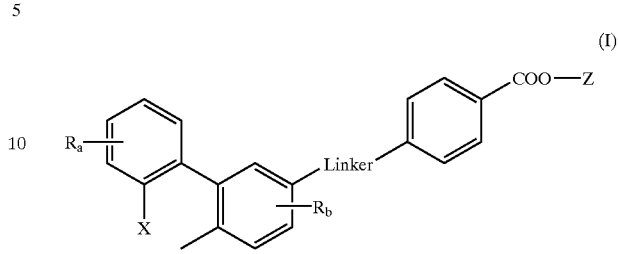

or a nontoxic pharmaceutically acceptable salt, physiologically hydrolyzable ester or solvate thereof, wherein $R_a$ and $R_b$ are independently selected from the group consisting of hydrogen, halogen, hydroxy, nitro, amino, mercapto, CF$_3$, $C_{1-6}$ alkyl, halosubstituted $C_{1-6}$ alkyl, hydroxy-substituted $C_{1-6}$ alkyl, aminosubstituted $C_{1-6}$ alkyl, $C_{1-6}$ alkoxy, $C_{1-6}$ alkylthio, formyl, carboxyl, mono- or di-$C_{1-6}$ alkyl-substituted amino, aryl or heteroaryl;

Linker is selected from the group consisting of —CH=CH—, —C≡C—, —C(=O)—NH—, —NH—C(=O)—, —CH$_2$O—, —O—C(=O)—, —C(=S)—NH—, —C(=O)—O—, —C(=O)—S—, —S—C(=O)—, —S—CH$_2$—, —CH$_2$—CH$_2$—, —CH$_2$—NH—, —C(=O)—CH$_2$—, —NH—C(=S)—, —CH$_2$S—, —OCH$_2$—, —NHCH$_2$— or CRc=CRd-, where Rc and Rd are independently hydrogen or $C_{1-6}$ alkyl;

X is —C(R)$_2$Y— or —YC(R)$_2$—, where Y is selected from the group consisting of O, S and C(R)$_2$; or X is selected from the group consisting of O, S, C(R)$_2$, and C=O (5-membered ring), wherein R is hydrogen or methyl; and Z is hydrogen or $C_{1-6}$ alkyl.

Definitions

As used herein, the term "alkyl" includes cyclic, branched and straight chain saturated aliphatic hydrocarbon groups having the specified number of carbon atoms, such as methyl, ethyl, propyl, isopropyl, butyl, sec and tert-butyl, pentyl, hexyl, heptyl, cyclopropyl, cyclobutyl, cyclopentyl, cyclohexyl, cycloheptyl, 2-methylcyclopropyl, cyclopropylmethyl, octyl, nonyl, norbornyl, undecyl, dodecyl, tridecyl, tetradecyl, pentadecyl, eicosyl, 3,7-diethyl-2,2-dimethyl-4-propylnonyl, cyclododecyl, adamantyl, and the like. Alkyl groups may be substituted with substituents, such as, halo, amino, hydroxy, alkoxy, cycloalkoxy, heterocyclooxy, alkylamino, arylamino, aralkylamino, cycloalkylamino, heterocycloamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido, e.g. SO$_2$NH$_2$, substituted sulfonamido, nitro, cyano, carboxy, carbamyl, e.g. CONH$_2$, substituted carbamyl e.g. CONH alkyl, CONH aryl, CONH aralkyl or cases where there are two substituents on the nitrogen selected from alkyl, aryl or aralkyl; alkoxycarbonyl, aryl, substituted aryl, guanidino and heterocycles, such as, indolyl, imidazolyl, furyl, thienyl, thiazolyl, pyrrolidyl, pyridyl, pyrimidyl and the like.

The term "polyfluoroalkyl" means that at least one hydrogen atom in an alkyl side-chain is replaced by a fluorine atom.

The term "amino", herein alone or as part of another group refers to —NH$_2$. An "amino38 may optionally be substituted with one or two substituents, which may be the same or different, such as alkyl, aryl, arylalkyl, alkenyl, alkynyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may be further substituted with a carboxylic acid or any of the alkyl or aryl substituents set out herein.

The term "alkenyl" defines a carbon chain having at least one double bond. For example, C$_{2-6}$ alkenyl refers to a straight or branched chain of two to six carbons bearing at least one double bond, such as ethenyl, 1-methyl-ethenyl, 1- or 2-propenyl, 1-methyl-1-propenyl, 1-methyl-2-propenyl, 1,1-dimethyl-2-propenyl, 2-methyl-2-propenyl, 1-, 2- or 3-butenyl, 1-methyl-1-butenyl, 2-methyl-1-butenyl, 3-methyl-1-butenyl, 3,3-dimethyl-1-butenyl, 1,2,3-dimethyl-1-butenyl, 1-methyl-2-butenyl, 1,1-dimethyl-2-butenyl, 2-methyl-2-butenyl, 3-methyl-2-butenyl, 1,3-butadienyl, 1,3-dimethyl-1,3-butadienyl, 1-, 2-, 3- or 4-pentenyl and the like. Alkenyl groups may be substituted with groups such as halo, alkoxy, cycloalkoxy, heterocyclooxy, arylamino, heterocycloamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido, e.g. SO$_2$NH$_2$, substituted sulfonamido, nitro, cyano, carboxy, carbamyl, e.g. CONH$_2$, substituted carbamyl e.g. CONH alkyl, CONH aryl, CONH aralkyl or cases where there are two substituents on the nitrogen selected from alkyl, aryl or aralkyl; alkoxycarbonyl, aryl, substituted aryl, guanidino and heterocycles, such as, indolyl, imidazolyl, furyl, thienyl, thiazolyl, pyrrolidyl, pyridyl, pyrimidyl and the like.

The term "alkynyl" defines a carbon chain having at least one triple bond. For example, C$_{2-6}$ alkynyl refers to a straight- or branched-chain of two to six carbons bearing at least one triple bond, such as ethynyl, 1- or 2-propynyl, 1-methyl-2-propynyl, 1,1-diemthyl-2-propynyl, 1-, 2- or 3-butynyl, 3-methyl-1-butynyl, 3,3-dimethyl-1-butynyl, 1-methyl-2-butynyl, 1,1-dimethyl-2-butynyl, 1-, 2-, 3, or 4-pentynyl and the like.

The term "C$_{3-6}$ cycloalkyl" refers to cyclopropyl, cyclobutyl, cyclopentyl or cyclohexyl radicals.

The terms "C$_{1-6}$ alkoxy" and "C$_{1-6}$ alkylthio" refer to an ether or a thioether bearing a straight or branched carbon chain, such as methoxy, methylthio, ethoxy, ethylthio, n-propoxy, n-propylthio, isopropoxy, isopropylthio, n-butoxy, n-butylthio, tert-butoxy, tert-butylthio, n-pentoxy, n-pentylthio and the like. The terms "halogen" or "halo" refer to fluorine, chlorine, bromine or iodine. The term "aryl" as used herein and in the text includes mono-, bi- and polycyclic aromatic groups such as phenyl, naphthyl, anthracyl, phenanthryl, biphenyl, binaphthyl and the like.

The term "heteroaryl" as used herein includes mono-, bi- and polycyclic aromatic heterocyclic groups containing 1 to 4 O, N or S atoms: preferred are 5- and 6-membered heterocyclic groups such as thienyl, furyl, thiadiazolyl, oxadiazolyl, triazolyl, isothiazolyl, thiazolyl, imidazolyl, isoxazolyl, tetrazolyl, oxazolyl, pyridyl, pyrazinyl, pyrimidinyl, pyridazinyl, pyrrolyl, pyrazolyl, and the like and fused 5,6-membered and 6,6-membered heterocyclic groups such as benzofuranyl, isobenzofuranyl, benzothienyl, indolyl, isoindolyl, indazolyl, indolizinyl, iosquinolyl, quinolyl, naphthyridinyl, quinoxalinyl, quinazolinyl, pteridinyl and the like.

Some compounds represented by formula I may also form pharmaceutically acceptable metal and amine salts in which the cation does not contribute significantly to the toxicity or biological activity of the salt. These salts are also part of the present invention. Suitable metal salts include the sodium, potassium, calcium, barium, zinc, and aluminum salts. The sodium or potassium salts are preferred. Amines which are capable of forming stable salts with the compounds represented by formula I include trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or other pharmaceutically acceptable amines.

Since compounds of formula I contain a carboxy group, they can form physiologically hydrolyzable esters which serve as prodrugs by being hydrolyzed in the body to yield formula I compounds per se. They are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include C$_{1-6}$ alkyl benzyl, 4-methoxybenzyl, indanyl, phthalilyl, methoxymethyl, C$_{1-6}$ alkanoyloxy-C$_{1-6}$ alkyl, e.g. acetoxymethyl, pivaloyloxymethyl or propionyloxymethyl, C$_{1-6}$ alkoxycarbonyloxy-C$_{1-6}$ alkyl, e.g. methoxycarbonyloxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters are prepared by conventional techniques known in the art.

The structural formulae as drawn in the instant application are believed to best represent the structures of compounds of the present invention. However, some compounds within the scope of the invention may exist as other tautomeric forms, in which hydrogen atoms are transposed to other parts of the molecules and the chemical bonds between the atoms of the molecules are consequently rearranged. It should be understood that the structural formulae represent all tautomeric forms, insofar as they may exist.

Some of the compounds of the present invention may have trans and cis (E and Z) isomers. In addition, the compounds of the present invention may contain one or more chiral centers and therefore may exist in enantiomeric and diastereomeric forms. The scope of the present invention is intended to cover all such isomers per se, as well as mixtures of cis and trans isomers, mixtures of diastereomers and racemic mixtures of enantiomers (optical isomers). In the present application, when no specific mention is made of the configuration (cis, trans or R or S) of a compound (or of an asymmetric carbon) then a mixture of such isomers, or either one of the isomers is intended.

As used herein and in the reaction schemes, the term "Grignard type reaction" is intended to include the addition of an organometallic compound to a carbonyl-containing compound. This includes addition of Grignard reagents, alkyl or aryllithiums, alkylzinc, alkylaluminum, organotitanium, organozirconium or organocerium compounds in an inert organic solvent such as ethyl ether, tetrahydrofuran, dichloromethane, benzene or toluene and the like. In certain instances, the complexation of the ketone or the Grignard reagent with cerium halides, perchlorate salts or tetraalkylammonium halides is necessary to improve the addition reaction. The term "Grignard type reaction" is also intended to include the addition of a Grignard reagent to an acid chloride that has been first reacted with tributylphosphine to form the corresponding phosphonium salt. The reaction is performed in an inert organic solvent such as ethyl ether, tetrahydrofuran, benzene and the like.

As used herein and in the reaction schemes, the term "Friedel-Crafts reaction" is intended to include the acylation or alkylation of aromatic rings. The acylation includes the addition of an acyl halide, a carboxylic acid, an anhydride or a ketene to an aromatic ring under Lewis acid conditions such as aluminum, tin, antimony, zirconium, or boron halides and the like or under proton acid conditions such as polyphosphoric acid, sufluric acid, methanesulfonic acid and the like. The alkylation includes the addition of alkyl halides, olefins or alcohols under Lewis or proton acid conditions such as those listed above.

The term "aromatic halogenation" is intended to include the addition of chlorine, bromine or iodine to an aromatic ring in presence or absence of a catalyst, usually iron or a Lewis acid such as aluminum, tin, or antimony halides and the like. It is also intended to include the reaction of N-chloro and N-bromoamides catalyzed by the addition of acids. For iodination, iodine may be used in the presence of an oxidizing agent such as nitric acid, iodic acid, sulfur trioxide or hydrogen peroxide or in the presence of copper salts, silver trifluoromethanesulfonate or thallium(I) acetate. Iodine monochloride can also be used.

As used herein and in the reaction schemes the term "reduction" is intended to include well-known reduction procedures of ketone groups by the use of aluminum or boron hydrides such as lithium aluminum hydride, aluminuim hydride, diisobutylaluminum hydride, sodium borohydride, sodium cyanoborohydride and the like in an inert organic solvent such as tetrahydrofuran, ethyl ether, ethanol, dichloromethane and the like. The term "reduction" is also intended to include the reduction or desulfurization of dithioacetals by the use of Raney nickel with or without hydrogen in organic solvents such as methanol, ethanol, ethanol/water, ethanol/ethyl ether, dioxane, acetone, tetrahydrofuran benzene and the like. Other conditions to perform hydrogenolysis are the use of trialkyltin hydrides in the presence of AIBN in an inert organic solvent such as benzene or toluene, or the use of aluminum or boron hydride such as lithium aluminum hydride or sodium borohydride in the presence of titanium(IV) chloride or nickel(II) chloride in tetrahydrofuran, ethanol or dimethylformamide.

The term "reduction" is also intended to include well-known reduction procedures of benzylic alcohols. These methods include the use of aluminum, boron or trialkylsilyl hydrides such as lithium aluminum hydride, sodium borohydride, sodium cyanoborohydride or triethylsilylhydride with or without aluminum chloride, zinc iodide or an acid such as hydrochloric acid, trifluoroacetic acid or trifluoroboron etherate in an inert organic solvent such as tetrahydrofuran, ethyl ether or ethanol. Well-known hydrogenolysis procedures using hydrogen with a catalyst such as palladium on charcoal or Raney nickel in methanol, or ethanol may also be used if appropriate.

As used herein and in the reaction schemes, the term "reductive amination" is intended to include conventional imine formation procedures well-known to those skilled in the art. These procedures involve the reaction of an amine with a Lewis acid such as titanium(IV) chloride or isopropoxide. Subsequently, this imine is reduced with well-known reductive agents such as sodium borohydride or sodium cyanoborohydride.

As used herein and in the reaction schemes, the term "hydrolysis" is intended to include conventional hydrolysis procedures of esters well-known to those skilled in the art. For example, methyl or ethyl esters may be removed by the use of aqueous solutions of sodium or potassium alkoxides in tetrahydrofuran or ethanol. The hydrolysis of tert-butyl esters are carried out under acidic conditions such as 90% trifluoroacetic acid or 6N hydrochloric acid in solvents such as tetrahydrofuran or dichloromethane. Allyl esters may be removed by the use of Pd(0) catalyst such as sodium acetate, potassium or sodium 2-ethylhexanoate, pyrolidine or morpholine and the like in an organic solvent such as acetonitrile, tetrahydrofuran, dichloromethane and the like. Finally, silyl esters such as trimethylsilylethyl esters may be cleaved by the use of tetrabutylammonium fluoride in tetrahydrofuran. The term "hydrolysis" is also intended to include conventional hydrolysis procedures of carbonyl protecting groups. For example, the hydrolysis of ketals and acetals may be carried out under acidic conditions such as 1N hydrochloric acid, 80% acetic acid or p-toluenesulfonic acid in solvents such as tetrahydrofuran or acetone.

As used herein and in the reaction schemes, the term "enol triflate or enol formation" is intended to include conventional and well-known enolate formation procedures and subsequent trapping of this enolate by the well-known triflating or silylating agents. Thus the ketones are treated with an organic base such as 2,6-di-tert-butyl-4-methylpyridine, sodium hydride, potassium hydride, lithium diisopropylamide or lithium bis(trimethylsilyl)amide in an inert organic solvent such as tetrahydrofuran, dimethylformamide or dichloromethane and the like. The resulting enolates are then reacted with triflic anhydride or 2-[N,N-bis(trifluoromethylsulfonyl)amino]pyridine and the like or an alkylsilyl halide or triflate.

As used herein and in the reaction schemes, the term "cross-coupling" is intended to include all the cross-coupling methods well-known by those skilled in the art that involve the reaction of a vinyl or aromatic triflate, bromide or iodide with a tin, zinc, magnesium or boronic derivative catalyzed by a palladium(0) or palladium(II) catalyst such as tetrakis(triphenyl-phosphine)palladium(0), bis(triphenylphosphine)palladium(II) chloride, palladium(II) acetate, tris(dibenzylidene-acetone)dipalladium(0), bis(diphenylphosphineferrocene)palladium(II) chloride and the like or a nickel(0) or nickel(II) catalyst such as tetrakis(triphenylphosphine)nickel(0), bis(triphenylphosphine)nickel(II) chloride and the like. Very often, as known by those skilled in the art, copper iodide, lithium chloride, zinc chloride or triphenylarsine, tris(2-furyl)phosphine or tris(2, 4,6-trimethoxyphenyl)phosphine must be added. When a boronic acid derivative is used, the reaction proceeds only in the presence of an inorganic base such as potassium phosphate or carbonate or sodium carbonate. These reactions are performed in an inert organic solvent such as dioxane, N-methylpyrrolidone, dimethylformamide, dimethoxyethane, tetrahydrofuran, toluene, benzene and the like.

As used herein and in the reaction schemes, the term "Heck coupling" is intended to include all known vinylations of alkenes or alkynes. Thus, a vinyl or aromatic triflate, bromide or iodide reacts with various substituted or non-substitued alkenes or alkynes in the presence of a trialkylamine base or an inorganic base such as potassium carbonate, sodium acetate and the like and a catalytic amount of Pd(II) complex such as palladium(II) acetate, bis(triphenylphosphine)palladium(II) chloride or bis(acetonitrile)palladium(II) chloride. Sometimes phosphine ligands such as triphenylphosphine, tritolylphosphine, diphenylphosphineferrocene or 1,3-bis(diphenylphosphino) propane and the like may facilitate the reaction.

As used herein and in the reaction schemes the term "alkylation" is intended to include conventional and well-known alkylation procedures. Thus, the desired alcohol or ketone groups which are to be alkylated are treated in the presence of an organic or inorganic base such as sodium hydride, potassium hydride, lithium diisopropylamine or lithium bis(trimethylsilyl)amide in an inert organic solvent such as tetrahydrofuran, dimethylformamide, hexamethylphosphoramide, dimethylsulfoxide, N-methylpyrolidinone and the like. Then an alkylating agent such as an alkyl, allyl or benzyl halide, mesylate or tosylate is added to this generated enolate, phenolate or thiophenolate. As used herein and in the reaction schemes the term "reductive alkylation" is intended to include the methods used to convert a tertiary alcohol to an alkyl, aryl or allyl group. Thus, the alcohol that has to be transformed may be treated by an organosilicon compound in the presence of boron trifluoride in dichloromethane or by a trialkylboron in the presence of trifluoromethanesulfonic acid in 1,1,2-trichlorotrifluoroethane. Another method is to react the corresponding alkoxide with iron pentacarbonyl to perform a deoxygenation reaction which may be worked-up by various alkyl or aryl halides. The alkoxide may be generated by treatment with a metal such as potassium, sodium or lithium in toluene.

As used herein and in the reaction schemes the term "oxidation" is intended to include conventional allylic oxidation methods such as selenium dioxide with or without the use of tert-butyl peroxide, sodium peroxide in ethanol and chromium(VI) reagents such as chromium(VI) trioxide in acetic acid and pyridinium dichromate and preferably potassium bromate in presence of ceric ammonium nitrate in dioxane.

As used herein and in the reaction schemes the term "aromatic substitution" is intended to include, in addition to the classic electrophilic reactions, nucleophilic substitutions of aromatic halides by water in the presence of sulfuric acid or trifluoroacetic acid, by alkoxides, aryloxides, thioalkoxides or thioaryloxides in an inert organic solvent such as hexamethylphosphoramide, dimethylsulfoxide, dimethylformamide and the like. The reaction of aryl halides with alkoxides may be promoted by copper salts and the reaction with thioalkoxides may be catalyzed by Pd(0) salts such as tetrakis(triphenylphosphine)palladium(0).

As used herein and in the reaction schemes the term "enone formation" is intended to include the well-known dehydrogenation procedures of ketones. Preferably, the ketone to be dehydrogenated is converted to a silyl enol ether as described above and then treated with an oxidizing agent such as dichlorodicyanoquinone, triphenylmethylcation or palladium(II) acetate in an inert organic solvent such as acetonitrile or dichloromethane.

As used herein and in the reaction schemes the term "Michael addition" is intended to include all conventional methods of conjugate addition of organometallic compounds or anions formed from malonates, cyanoacetates, acetoacetates, β-ketoesters, esters, ketones, alkehydes, nitriles, nitro compounds, sulfones and the like to an α,β-unsaturated ketone. The organometallic compounds include lithium dialkylcopper, organoaluminum, trialkylzinc lithium, arylpalladium, arylmercury, borane reagents and the like. The inert organic solvents used may be tetrahydrofuran, dioxane, dimethylformamide, dichloromethane, benzene and the like.

As used herein and in the reaction schemes, the term "acid halide formation" is intended to include the well-known methods of the conversion of a carboxylic acid to an acid halide such as the use of thionyl chloride, oxalyl chloride or bromide in presence of dimethylformamide in dichloromethane and phosphorus trichloride or tribromide.

As used herein and in the reaction schemes, the term "Wittig type reaction" is intended to include conventional methods of Homer-Emmons, Nysted or Wittig olefination reactions of aldehydes or ketones. Thus, in a Homer-Emmons olefination, an alkyl or aryl phosphonate is treated with a base such as sodium hydride, lithium diisopropylamide or lithium bis(trimethylsilyl)amide and the like in an inert organic solvent such as tetrahydrofuran, dichloromethane, benzene and the like and reacted with a ketone or an aldehyde. In a Wittig reaction, an alkyl or arylphosphonium salt is treated with a base such as butyllithium, lithium diisopropylamine or lithium bis(trimethylsilyl)amide and the like in an inert organic solvent such as tetrahydrofuran, dichloromethane, benzene and the like and reacted with a ketone or an aldehyde. In a Nysted olefination, the ketone is treated with {cyclo-dibromodi-$\mu$-methylene[$\mu$-(tetrahydrofuran)]trizinc} (Nysted reagent) in the presence of titanium chloride in an inert solvent such as tetrahydrofuran and dichloromethane.

As used herein and in the reaction schemes, the term "epoxidation or thioepoxidation" is intended to include the well-known methods of epoxide formation by reaction of an olefin with a per-acid as well as epoxide formation by reacting a gem-dihalide in presence of a strong base such as butyllithium, t-butyllithium methyllithium or lithium with a ketone in inert organic solvents such as tetrahydrofuran or ether. It is also intended to include methods using the reaction of sulfur ylides such as dimethyloxosulfonium methylide and dimethylsulfonium methylide which are generated by treatement of the corresponding sulfonium salt with an organic base such as sodium hydride or potassium tert-butoxide in organic solvents such as dimethylsulfoxide, tetrahydrofuran, t-butanol, dimethoxyethane and the like with a ketone. The term "epoxidation or thioepoxidation" is also intended to include the methods by which a diazoalkane reacts with a ketone in solvent such as methanol or ethyl ether.

As used herein and in the reaction schemes, the terms "acetal, ketal, thioacetal or thioketal formation" are intended to include processes well-known in the art and they are well illustrated in "Protective Groups in Organic Synthesis", Second Ed., T. W. Green and P. G. W. Wuts, John Wiley & Sons, New York, 1991, Chapter 4 and references therein. Thus, the ketone or aldehyde that has to be reacted is treated with the desired alcohol or diol, thiol or dithiol in the presence of an inorganic or organic acid such as p-toluenesulfonic acid, hydrochloric acid, trifluoroboron etherate, oxalic acid, adipic acid, pyridinium tosylate, acetic acid and the like, in inert organic solvents such as benzene, toluene, acetonitrile or dichloromethane.

As used herein and in the reaction schemes, the term "cyclopropanation" is intended to include the well-known Simmons-Smith procedure involving the reaction of a dihaloalkane and zinc-copper couple with an olefin in organic solvents such as ethyl ether, dimethoxyethane or tetrahydrofuran. The preparation of the zinc-copper couple is preferably carried out with zinc dust and cuprous chloride. Other variations of this procedure are the use of a dihaloalkane with samarium, mercuric chloride in tetrahydrofuran or with diethylzinc in dichloromethane or toluene. The term "cyclopropanation" is also intended to include the addition of carbenes to double bonds such as the reaction of a diazoalkane with rhodium acetate or palladium(II) acetate in tetrahydrofuran or dichloromethane, the reaction of a dihaloalkane with a strong base such as n-butyllithium, methyllithium or t-butyllithium in inert organic solvents such as ethyl ether or tetrahydrofuran or the reaction of chloroform with sodium or potassium hydroxide under phase transfer conditions such as tetraalkylammonium halide in water or a mixture of water/ethanol.

The term "imine formation" is intended to include the well-known procedures by which a ketone reacts with an amine in presence of an acid with or without a drying agent. These conditions include various inorganic and organic acids such as zinc chloride, titanium chloride, hydrochloric acid, sulfuric acid, trifluoroacetic acid, acetic acid, p-toluenesulfonic acid and the like in solvents such as dichloromethane, ethanol, benzene, toluene, tetrahydrofuran, dimethylformamide and the like.

Modes of Administration

The compounds of this invention may be administered systemically or topically, depending on the condition to be treated, the need for site-specific treatment or the quantity of drug to be administered.

In the treatment of skin-related diseases such as acne, it will generally be preferred to administer the drug topically, although oral administration may also be used for the treatment of severe acne or psoriasis. In the treatment of cancerous or precancerous conditions, the drug is preferably administered systemically.

The topical formulation used may be a solution, suspension, gel or ointment and the like. If the drug is to be administered systemically, it may be prepared as a powder, pill, tablet or the like or as a syrup suitable for oral administration. For intravenous or intraperitoneal administration, the compound will be prepared as a solution or suspension capable of being administered by injection.

Treatment of skin-related diseases or cancerous and precancerous conditions will be effected by administration of the therapeutically effective dose of one or more compounds of the present application. A therapeutic concentration will be the concentration which effects reduction of the condition or retards its expansion.

The compounds of formula I above may be used topically or systemically, as anticancer agents and in the treatment, amelioration or prevention of the skin disorders and rheumatic illnesses, such as, osteoarthritis, treatment of transplant rejections, psoriasis, psoriatic arthritis, inflammatory bowel disease, acute pancreatitis, and chronic pancreatitis (including rheumatoid arthritis) as described in U.S. Pat. No. 5,618,839. In this regard they may be used for therapy in animals, including humans, of premalignant epithelial cell lesions, as a prophylaxis against tumor promotion in epithelial cells and treatment for dermatoses such as ichthyoses, follicular disorders, benign epithelial disorders and other proliferative skin diseases such as psoriasis, eczema, atopic dermatitis, non-specific dermatosis and the like. They may also be used in reversing and preventing the effects of irradiation damage to skin. When used for the above purposes, they will usually be formulated with a pharmaceutically acceptable liquid, semi-solid, or solid carrier. A pharmaceutically acceptable carrier is a material that is nontoxic and generally inert and does not adversely affect the functionality of the active ingredients. Such materials are well known and include those materials sometimes referred to as diluents or vehicles (excipients) in the pharmaceutical formulation art. The carrier may be organic or inorganic in nature.

Examples of pharmaceutically acceptable carriers that may be used to formulate a compound of formula I are water, gelatin, lactose, starch, mineral oil, cocoa butter, dextrose, sucrose, orbital, mannitol, gum acacia, alginates, cellulose, talc, magnesium stearate, polyoxyethylene sorbitan monolaurate, and other commonly used pharmaceutical carriers. In addition to a compound of formula I and carrier, the formulation may contain minor amounts of additives such as flavoring agents, coloring agents, thickening or gelling agents, emulsifiers, wetting agents, buffers, stabilizers, and preservatives such as antioxidants.

The dosages and dosage regimen in which the compounds of formula I are administered will vary according to the dosage form, mode of administration, the condition being treated and particulars of the patient being treated. Accordingly, optimal therapeutic concentrations will be best determined at the time and place through routine experimentation.

In the treatment of dermatoses, it will generally be preferred to administer the drug topically, though in certain cases oral administration may also be used. If the compounds according to the invention are used topically, it will be found that they exhibit a good activity over a very broad range of dilution; in particular, concentrations of the active compound or compounds ranging from 0.0005% to 2% by weight can generally be used. It is of course possible to use higher concentrations if this should become necessary for a particular application; however, the preferred concentration of active principle are from 0.002% to 1% by weight.

For topical administration the compounds of formula I are conveniently provided in the form of unguents, gels, creams, ointments, powders, dyeing compositions, solutions, suspension, emulsions, lotions, sprays, adhesive plasters and impregnated pads. The compounds according to the invention can be mixed with inert nontoxic, generally liquid or pasty, bases suitable for topical treatment. Preparation of such topical formulations are well described in the art of pharmaceutical formulations as exemplified, for example, Remington's Pharmaceutical Science, Edition 17, Mack Publishing Company, Easton, Pa. Other medicaments can be added to such formulation for such secondary purposes as treating skin dryness, providing protection against light; other medications for treating dermatoses, preventing infection, reducing irritation, inflammation and the like.

The compounds according to the invention can also be used enterally. Orally, the compounds according to the invention are suitable administered at the rate of 100 µg to 100 mg per day per kg of body weight. The required dose can be administered in one or more portions. For oral administration, suitable forms are, for example, tablets, pills, dragees, syrups, suspensions, emulsions, solutions, powders and granules; a preferred method of administration consists in using pills containing from 1 mg to about 1000 mg of active substance.

U.S. Pat. No. 4,876,381 issued on Oct. 24, 1989 to Lang et al. provides examples of formulations constituting gel, unguent, powder, cream, and the like. The aforesaid U.S. patent can be used as a guide to formulate a compound of formula I and is herein incorporated by reference in its entirety.

Several retinoids have been found to possess anti-tumor properties. See, for example, Roberts, and Sporn, in "The Retinoids", Sporn, M. B., Roberts, A. B., and Goodman, D. S., eds, 1984, 2 pp. 209–286, Academic Press, New York; Lippman, et al. *Cancer Treat. Rep.,* 1987, 71, p. 391; ibid., p. 493.

As used herein, the term "anti-tumor" includes both chemopreventive (prophylactic or tumor promotion inhibiting) and therapeutic (curative) use. For example, all-trans retinoic acid can be used to treat acute promyelocytic leukemia. See, for example, Huang, et al., *Blood,* 1988, 72 p. 567. Isotretinoin has been shown to be useful in prevention of second primary tumors in squamous-cell carcinoma of the head and neck. Hong, W. K. et al., N. Engl. J. Med., 1990, 323 p. 795.

The compounds of formula I can be used in a substantially similar manner to other retinoids for treating (both chemopreventively and therapeutically) various tumors. For the compounds of this invention, the anti-tumor dose to be administered, whether a single dose, multiple dose, or a daily dose, will of course vary with the particular compound employed because of the varying potency of the compound, the chosen route of administration, the size of the recipient, the type of tumor, and the nature of the patient's condition. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. An oncologist skilled in the art of cancer treatment will be able to ascertain, without undue experimentation, appropriate protocols for the effective administration of the compounds of this present invention, such as by referring to the earlier published studies on retinoids found to have anti-tumor properties. For example, for the prevention of second primary tumors with a compound of formula I in squamous-cell carcinoma of the head and neck, an oncologist may refer to the study by Hong, et al. in *N. Engl. J. Med.,* 1990, 323, p. 795. For treating acute promyelocytic leukemia, the oncologist may refer to the study by Huang, et al. *in Blood,* 1988.

Compounds of the present invention are useful for the minimization or prevention of post-surgical adhesion formation between organ surfaces. The term "organ surface" is intended to encompass any internal organ of a living animal. including but not limited to the uterus, intestines, liver, kidneys, heart and lungs. For prevention of surgical adhesions, the compounds may be administered by a variety of systemic and local methods. The compounds may be administered orally, by intravenous injection, by intramuscular injection or by intracavity instillation. The general range of doses will depend on the efficacy of each compound and the intended route but is expected to be from 0.1 mg/kg to 100 mg/kg. Preferred routes of administration are oral administration or direct administration (intracavity instillation) to a site of surgical activity on an organ surface. For intracavity administration the retinoid can be administered in a suitable vehicle such as 5% dextrose in water adjusted to a pH to assure complete salt formation. However it is understood that many other single dose delivery systems could be contemplated by those skilled in the art including microcapsules, microspheres, liposomes, viscous instilates, and polymeric delivery materials. U.S. Pat. No. 6,319,948, incorporated herein by reference, describes the use of retinoid-like compounds for the treatment of post-surgical adhesion formation.

The synthesis of a compound of formula I can be accomplished by a wide variety of methods using conventional starting materials and processes. The synthetic descriptions and specific examples that follow are only intended for the purpose of illustration, and are not to be construed as limiting in any manner ways to make compounds of the present invention by other methods.

Typically a compound of formula I can be made by employing one of the processes or obvious variations thereof as depicted in Schemes I to III. All the steps in Schemes I to III are standard processes which can be easily practiced by anyone skilled in the art. The specific examples that are provided after the Schemes are intended to illustrate specific conditions which may be employed to carry out certain steps in the Schemes and are not to be construed as limiting the conditions in any way.

Synthetic Routes:

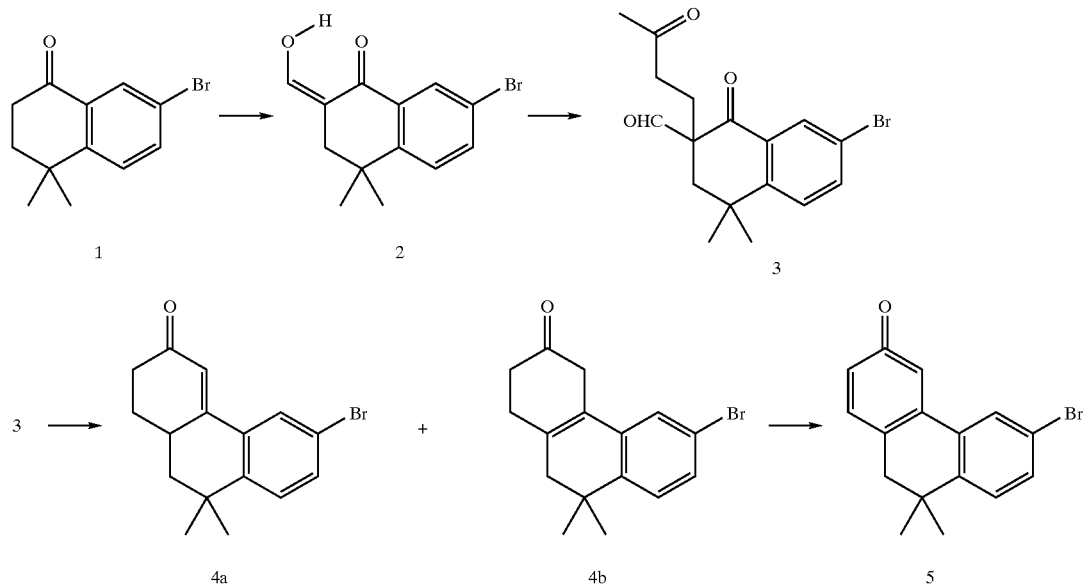

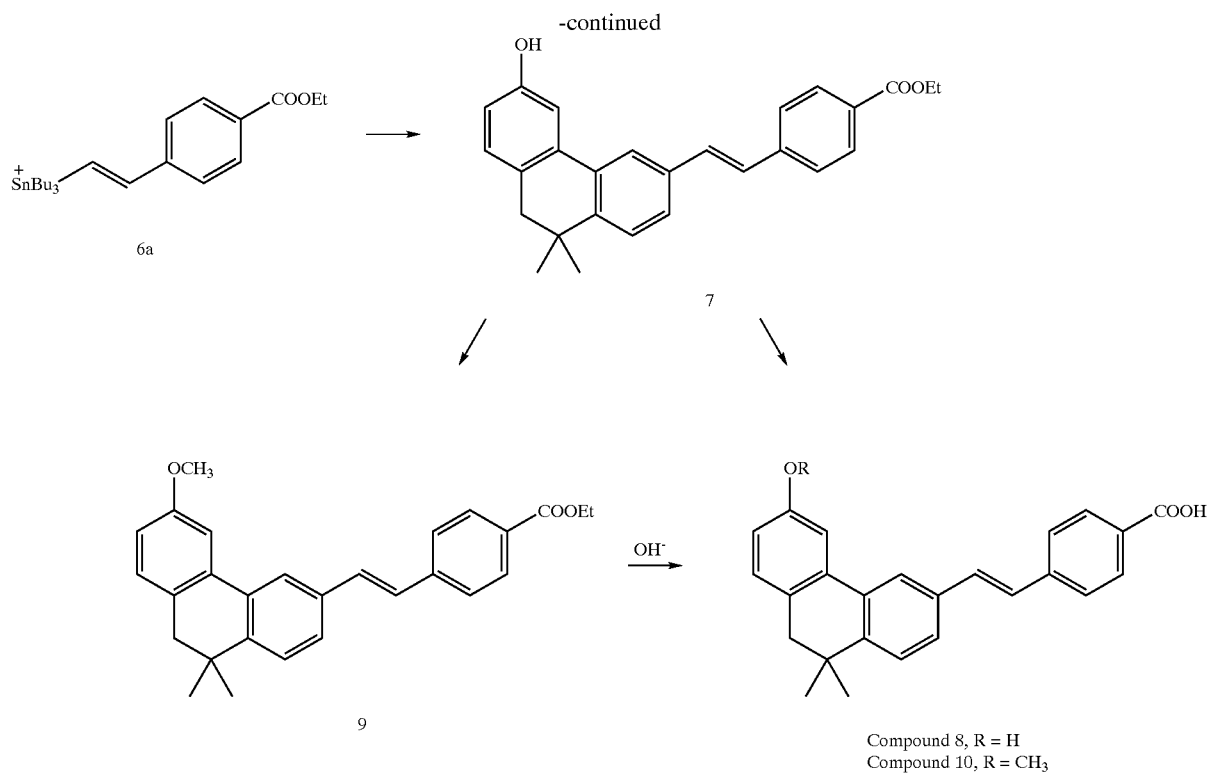

Compounds 8 and 10, where X=—CH$_2$C(CH$_3$)$_2$—, R=H (compound 8) or CH$_3$ (compound 10) and Linker=—CH=CH—, may be synthesized as shown in Scheme I. Known bromo-tetralone 1 (from J. Starrett et al; European patent application #661,259 (Jul. 5, 1995) or Y. Endo et al; *J Med Chem* 1998, 41, 1476–96) may be formylated, using, for example, ethyl formate in the presence of sodium hydride base in a suitable solvent such as benzene, to give hydroxymethylene compound 2. Compound 2 may be condensed under basic conditions with methyl vinyl ketone to give annulated derivative 3. 3 may then undergo a hydroxide-catalyzed ring closure and side-chain hydrolysis to give the mixture of enones 4a+4b. This mixture may then be aromatized at elevated temperature in the presence of a catalyst such as palladium chloride to give aromatized compound 5. 5 may undergo a Stille-type coupling with 6a to give ester 7, which can either be hydrolyzed directly to give final compound 8 or reacted with an alkylating agent such as methyl iodide to give the ether 9, which may then be hydrolyzed to give final compound 10. Similar compounds where Linker=—C≡C— may be synthesized by substituting reagent 6b for 6a in the sequence given above:

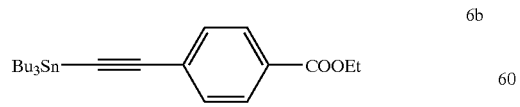

6b

For similar compounds where X=—C(CH$_3$)$_2$CH$_2$—, a similar synthetic sequence may be employed, as shown in Scheme II:

Scheme II

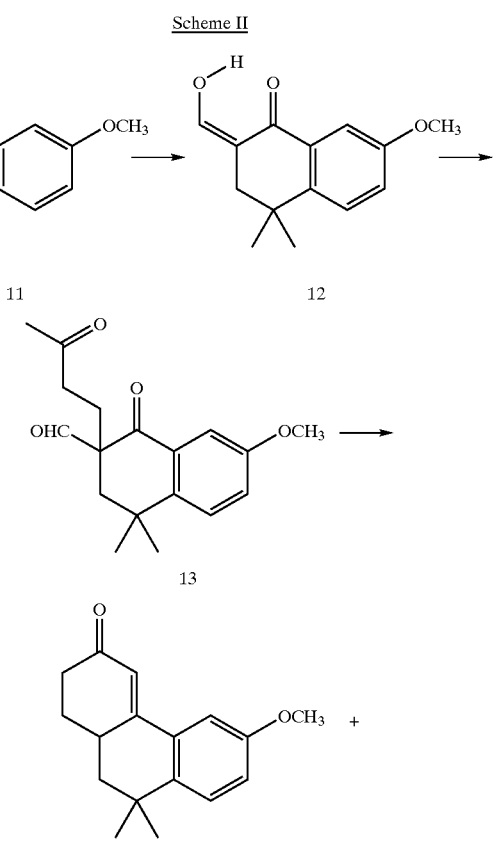

-continued

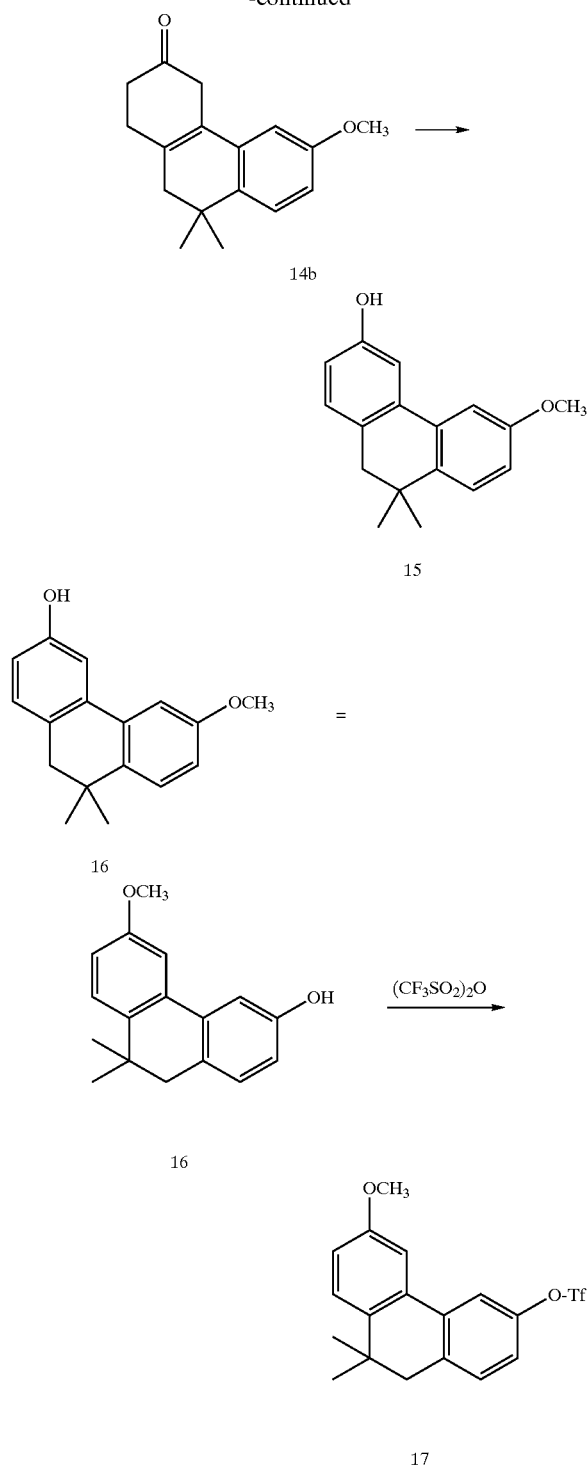

Starting from the known 11 (H. Hart et al; *J. Amer. Chem Soc.* 1963, 85, 3269–3273), the sequence is carried out in the same fashion up to intermediate 16, which can then be reacted with trifluoromethane sulfonic anhydride to produce the trifluoromethanesulfonate ("triflate", abbreviated "O-Tf"), 17, which can then be condensed with 6a or 6b, followed by hydrolysis of the ester, to give the corresponding final compound.

A more general route to general intermediates for compounds of the instant invention is shown diagrammatically in scheme III:

Scheme III

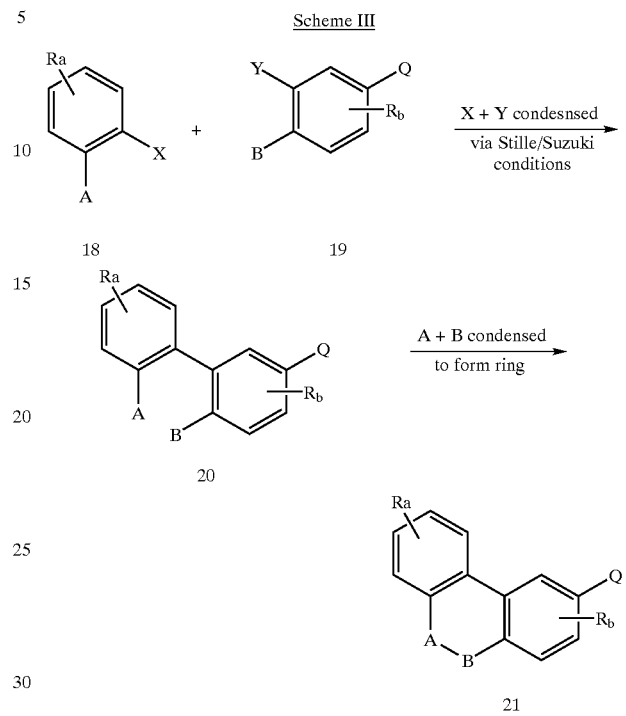

Monomeric intermediates 18 and 19, where either of X or Y is halogen or triflate and the other of X or Y is a stannane or borate functional group, may be condensed via metal catalysis, using a metal such as palladium, under Stille or Suzuki reaction conditions, to generate biphenyl intermediates 20. Proper choices of A and B allow ring closure in a subsequent step, yielding intermediates 21, where the A-B linkage is equivalent to X in Formula I.

For X=—C(CH$_3$)$_2$CH$_2$—, A may be H and B may be HO—C(CH$_3$)$_2$CH$_2$—, and the ring closure may be done under acid or Friedel-Crafts catalysis, using, for example, aluminum chloride as a catalyst. The functional group HO—C(CH$_3$)$_2$CH$_2$— is available using standard organic transformations from the corresponding methyl group (compounds 22 are well-known in the literature):

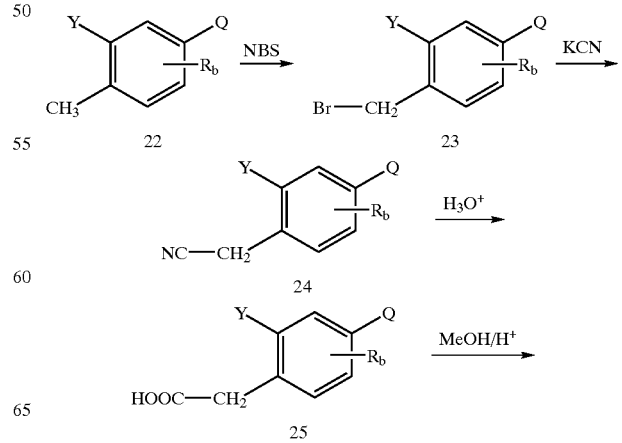

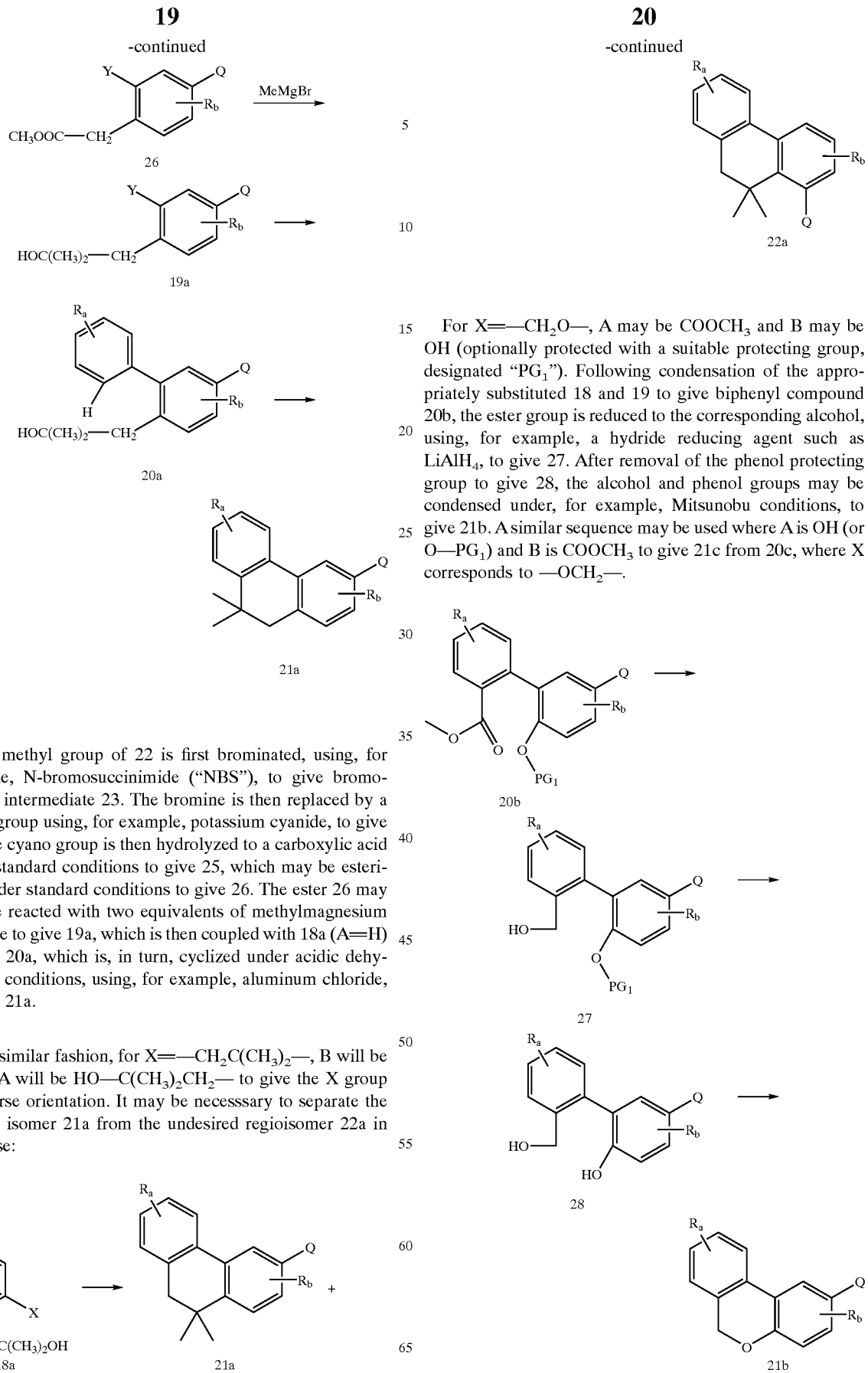

The methyl group of 22 is first brominated, using, for example, N-bromosuccinimide ("NBS"), to give bromomethyl intermediate 23. The bromine is then replaced by a cyano group using, for example, potassium cyanide, to give 24. The cyano group is then hydrolyzed to a carboxylic acid under standard conditions to give 25, which may be esterified under standard conditions to give 26. The ester 26 may then be reacted with two equivalents of methylmagnesium bromide to give 19a, which is then coupled with 18a (A=H) to give 20a, which is, in turn, cyclized under acidic dehydrating conditions, using, for example, aluminum chloride, to give 21a.

In a similar fashion, for X=—$CH_2C(CH_3)_2$—, B will be H and A will be HO—$C(CH_3)_2CH_2$— to give the X group in reverse orientation. It may be necesssary to separate the desired isomer 21a from the undesired regioisomer 22a in this case:

For X=—$CH_2O$—, A may be $COOCH_3$ and B may be OH (optionally protected with a suitable protecting group, designated "$PG_1$"). Following condensation of the appropriately substituted 18 and 19 to give biphenyl compound 20b, the ester group is reduced to the corresponding alcohol, using, for example, a hydride reducing agent such as $LiAlH_4$, to give 27. After removal of the phenol protecting group to give 28, the alcohol and phenol groups may be condensed under, for example, Mitsunobu conditions, to give 21b. A similar sequence may be used where A is OH (or O—$PG_1$) and B is $COOCH_3$ to give 21c from 20c, where X corresponds to —$OCH_2$—.

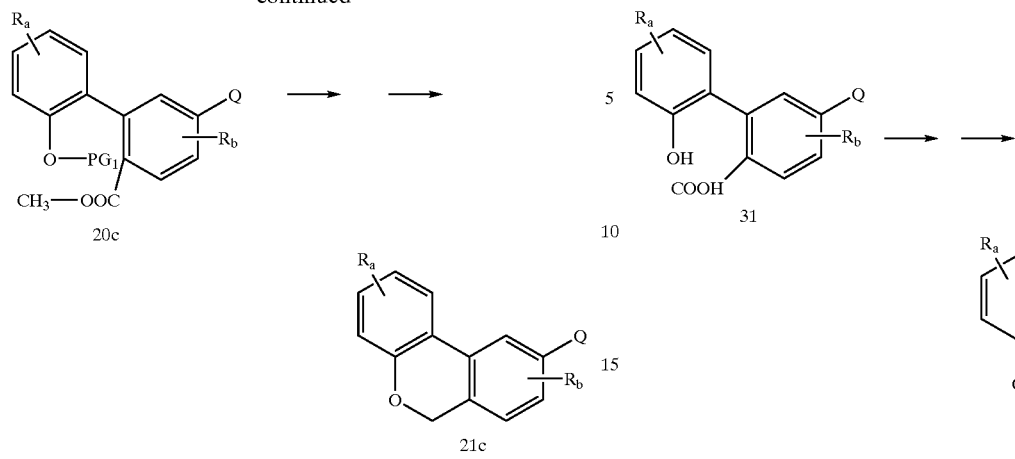

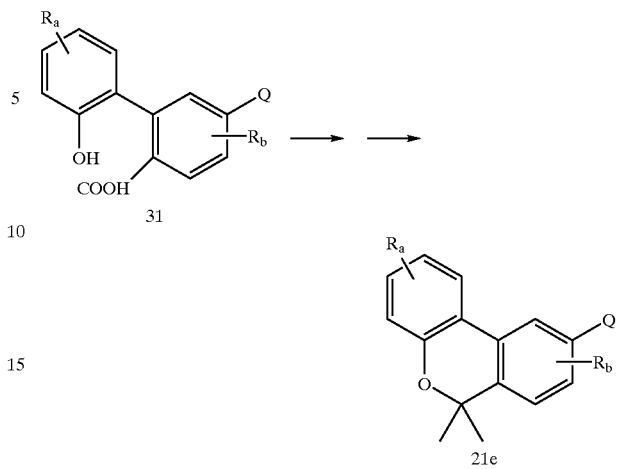

For X=—C(CH₃)₂O—, A may be COOH and B may be OH, and the following reaction sequence may be employed:

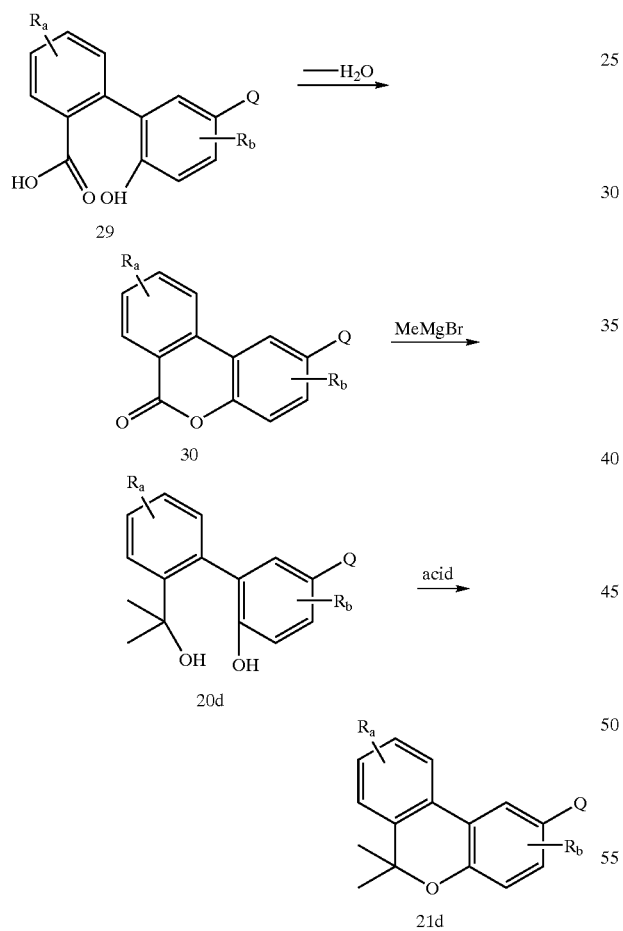

For X=—C(CH₃)₂S—, A may be COOH and B may be SH, and the following reaction sequence may be employed:

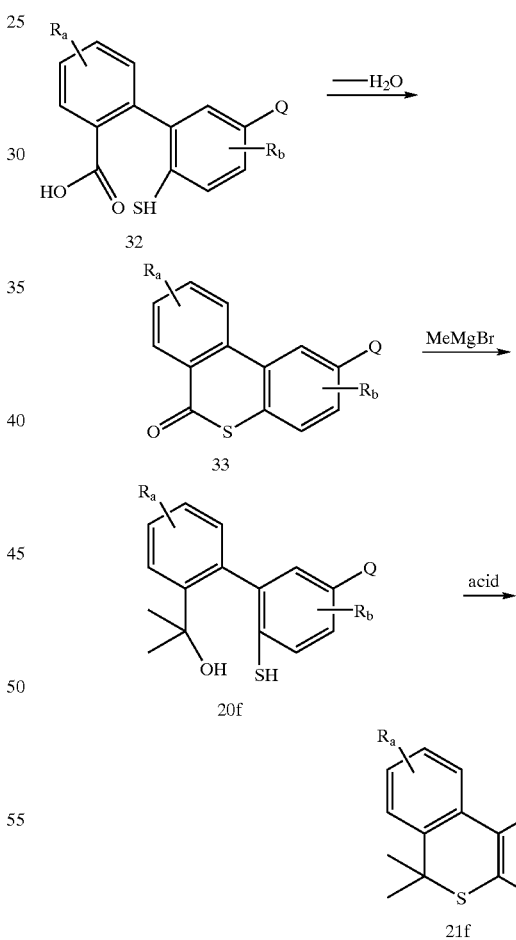

Intermediate 29 may be cyclized to lactone 30, using a dehydrating agent, and then reacted with two equivalents of methyl magnesium bromide to give ring-opened diol 20d. This compound may be re-cyclized under acid conditions to give 21d.

Similarly, for X=—OC(CH₃)₂—, A may be OH and B may be COOH, and an equivalent reaction sequence employed to give 21e from 31.

Intermediate 32 may be cyclized to thiolactone 33, using a dehydrating agent, and then reacted with two equivalents of methyl magnesium bromide to give ring-opened alcohol/thiol 20f, which may be re-cyclized under acid conditions to give 21f.

Similarly, for X=—SC(CH$_3$)$_2$—, A may be SH and B may be COOH, and an equivalent reaction sequence employed to give 21g from 34.

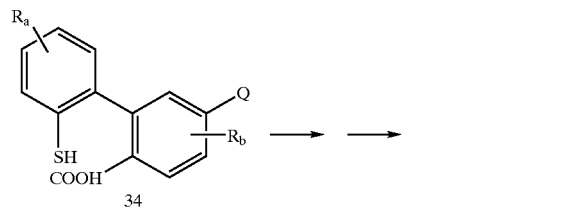

For X=—CH$_2$S—, A may be COOH and B may be SH, and the following reaction may be employed:

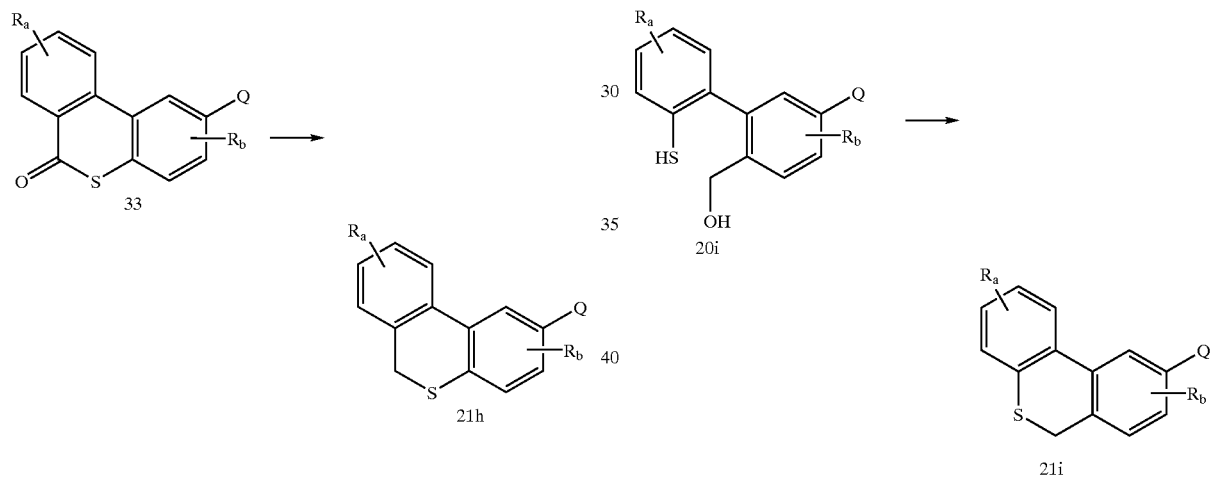

Intermediate 33, may be reduced, using, for example, lithium aluminum hydride, to give compound 21h directly. Alternatively, A may be CH$_2$OH and B may be SH, and the following reaction may be employed:

Compound 20h, available from the reduction of 32, may be cyclized using either acid or Mitsunobu-type conditions to give 21h.

Similarly, for X=—SCH$_2$—, A may be SH and B may be COOH, and an equivalent reaction employed to give 21i, or A may be SH and B may be CH$_2$OH, as above:

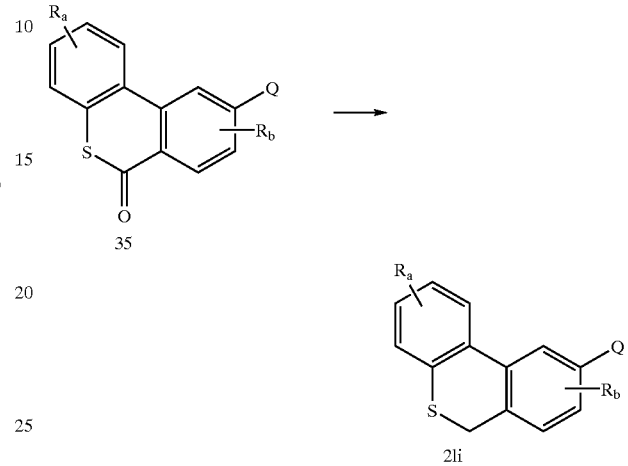

For X=C=O, CH$_2$, or C(R)$_2$, either of A or B may be COOH and the other of A or B is H. The following reaction sequence may be employed:

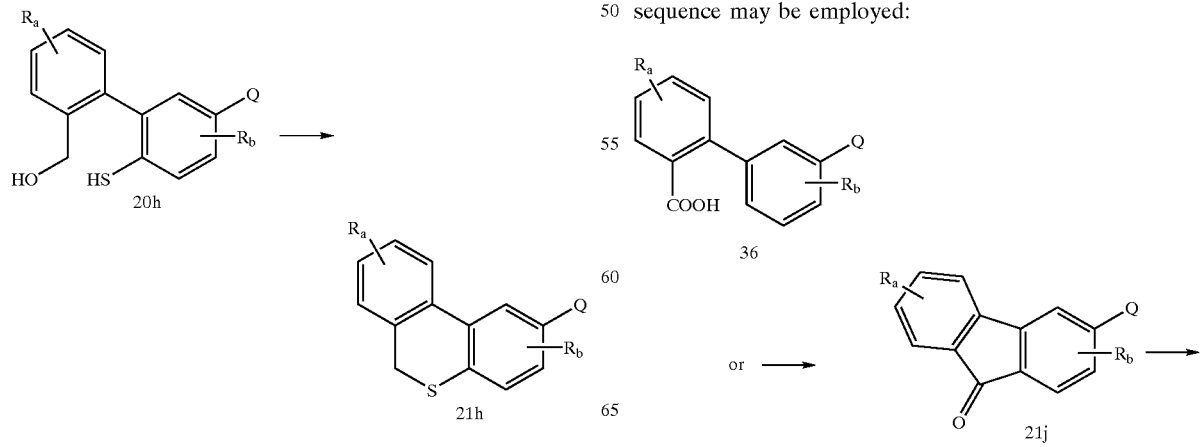

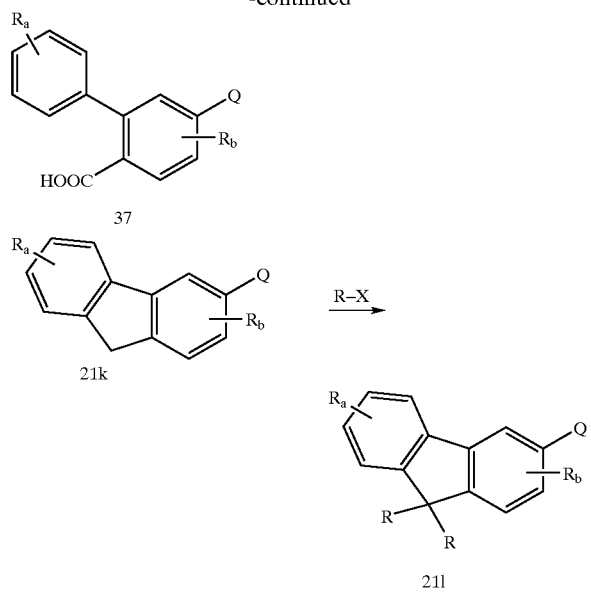

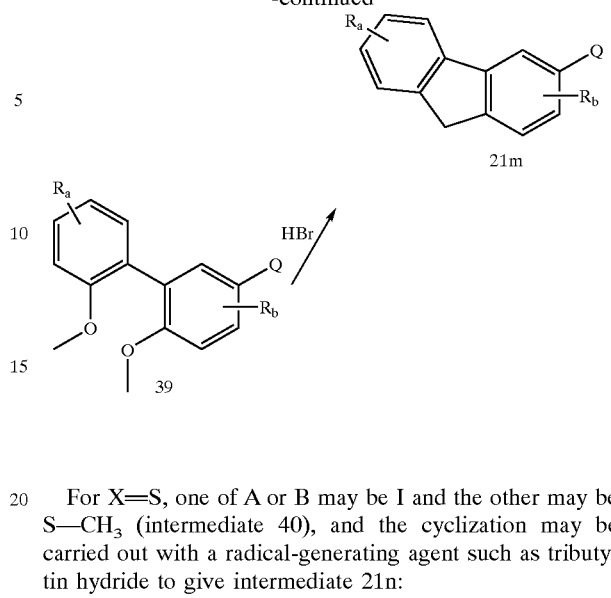

Either of acids 36 or 37 may be cyclized to give 21j (X=C=O) under Friedel-Crafts or dehydrating acid conditions. It may be advantageous to use 37, depending on the choice of $R_a$ and $R_b$, to minimize the formation of positional isomers. The ketone may be reduced under standard conditions to give 21k (X=CH$_2$), and the methylene group may be deprotonated using strong base followed by treatment with an excess of alkyl halide, R—X, to give 21, X=C(R)$_2$.

For X=O, A and B may both be OH (intermediate 38), and cyclization may be effected using a reagent such as stannous chloride, or A and B may both be OCH$_3$ (intermediate 39), and cyclization may be effected using a strong mineral acid such as HBr, to give 21m:

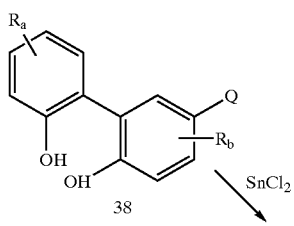

For X=S, one of A or B may be I and the other may be S—CH$_3$ (intermediate 40), and the cyclization may be carried out with a radical-generating agent such as tributyl tin hydride to give intermediate 21n:

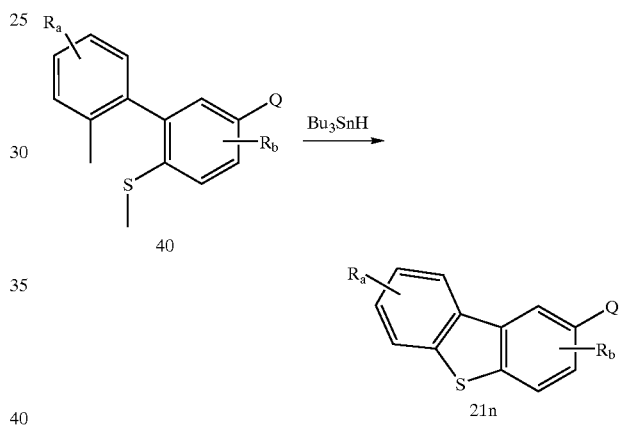

Intermediates 21(a-n) may then be employed in the synthesis of a wide variety of final products. For example, compounds 21 may be reacted with the known 41 to give, after hydrolysis, final products 42a (Linker=—CH=CH—) or with the known 43 to give, after hydrolysis, final products 42b (Linker=—C≡C—):

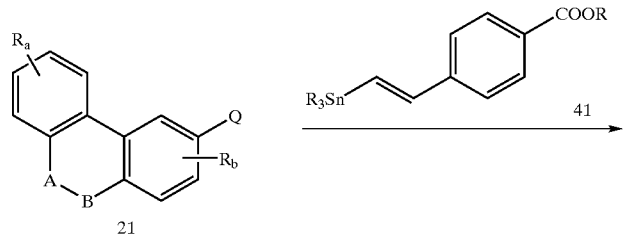

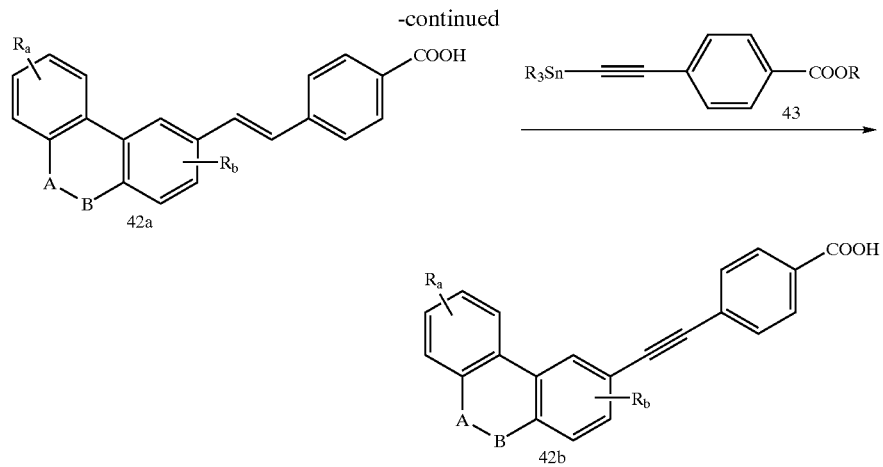

Alternatively, intermediates 21 may be carbonylated in the presence of carbon monoxide, palladium catalyst, and an alcohol, to give, after hydrolysis, acids 44:

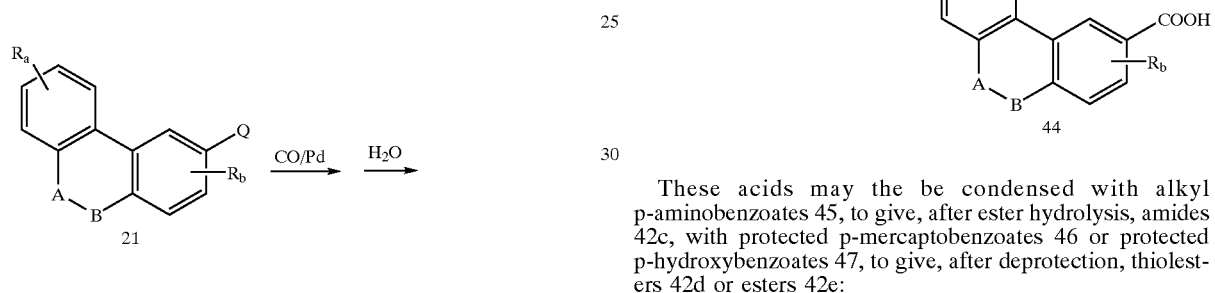

These acids may the be condensed with alkyl p-aminobenzoates 45, to give, after ester hydrolysis, amides 42c, with protected p-mercaptobenzoates 46 or protected p-hydroxybenzoates 47, to give, after deprotection, thiolesters 42d or esters 42e:

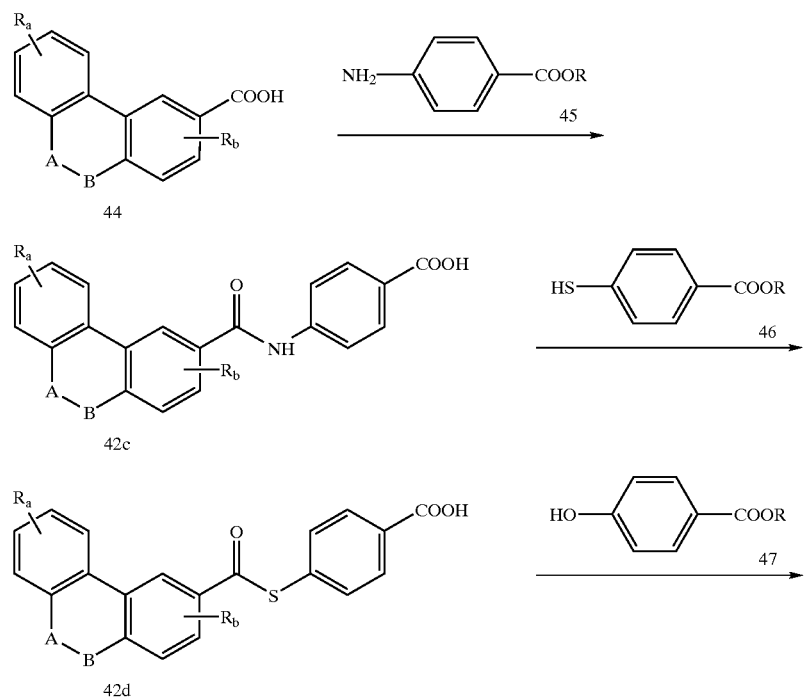

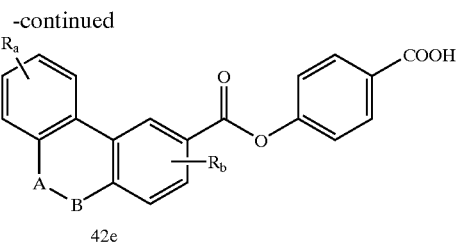
42e

Alternatively, acids 44 may be reduced to alcohols 48, which may then be converted to benzyl halides 49:

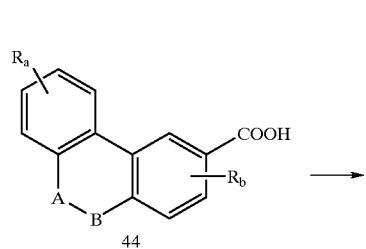
44

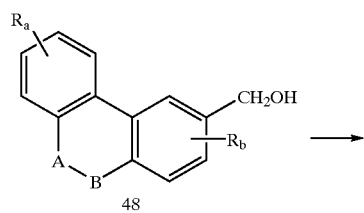
48

-continued

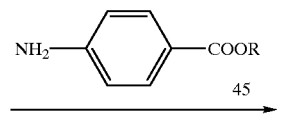
49

These benzyl halides 49 may then be reacted with alkyl p-aminobenzoates 45 to give, after ester hydrolysis, amines 42f, with alkyl p-mercaptobenzoates 46 to give, after ester hydrolysis, thioethers 42g, or with alkyl p-hydroxybenzoates 47 to give, after ester hydrolysis, ethers 42h:

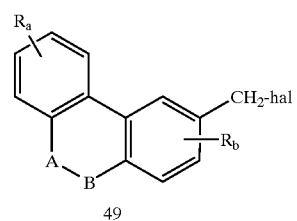
49

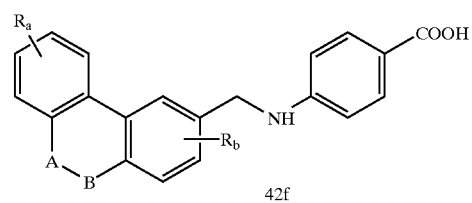
42f

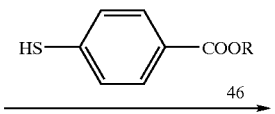
46

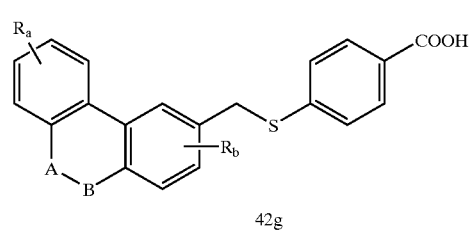
42g

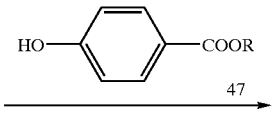
47

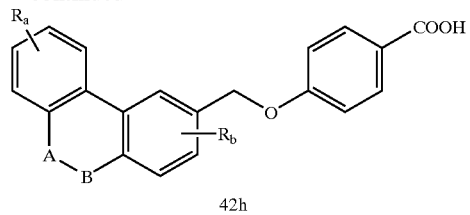

42h

The following non-limiting examples serve to illustrate the practice of the invention.

EXAMPLE 1

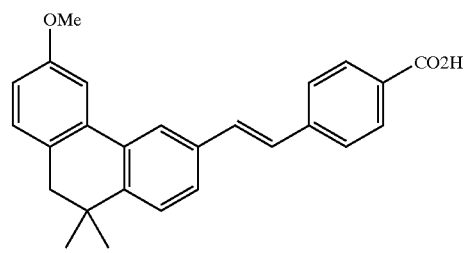

7-Bromo-4,4-dimethyl-2-formyl-1-oxo-1,2,3,4-tetrahydronaphthalene

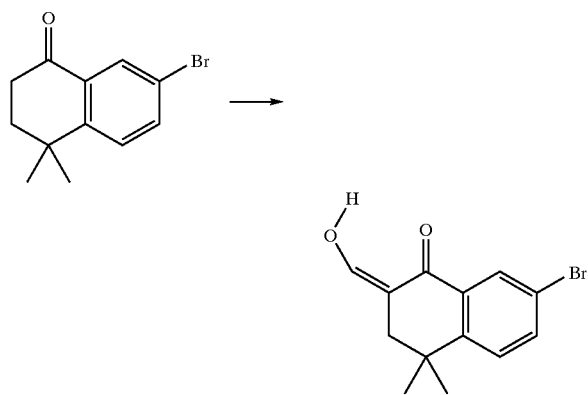

A solution of 7-bromo-4,4-dimethyl-1-oxo-1,2,3,4-tetrahydronaphthalene (2.0 g, 7.9 mmol) in benzene (34 ml) was added to a cold (0° C.) suspension of sodium hydride (60% in oil, 2.28 g, 57 mmol) and sodium methoxide (24 mgs) in benzene (34 ml). Ethyl formate (2.74 ml, 33.9 mmol) was then added dropwise and the mixture was stirred at 0° C. for 2 hours and then at room temperature for 3 hours. Wet methanol was then added and the aqueous phase was acidified with 4M hydrochloric acid and extracted with ethyl acetate (3×). The combined organic phases were washed with 2M sodium carbonate and the sodium carbonate phases were combined, acidified and reextracted with ethyl acetate. The combined organic phases were dried over anhydrous magnesium sulfate, concentrated and purified by silica gel chromatography (ethyl acetate/hexane 10:90) to give the title material (2.1 g, 95%).

$^1$H NMR (CDCl$_3$, δ, ppm): 1.26 and 1.31 (2×3H, 2 s, 2×—CH$_3$), 2.46 (2H, s, —CH$_2$-6), 7.27 (1H, d, H-4), 7.60 (1H dd, J=8.4 and 2.0 Hz, H-3), 8.10 (1H, d, J=2.0 Hz, H-1), 8.19 (1H, s, =CH—OH), 14.4 (1H, s, —OH).

EXAMPLE 2

7-Bromo-4,4-dimethyl-2-formyl-2-(3-oxo-butyl)-1-oxo-1,2,3,4-tetrahydronaphthalene

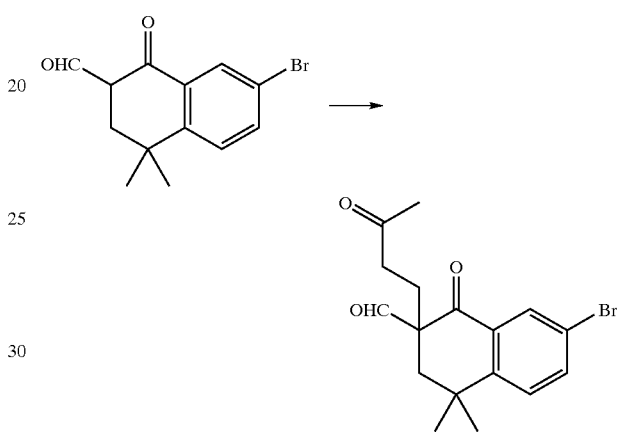

7-Bromo-4,4-dimethyl-2-formyl-1-oxo- 1,2,3,4-tetrahydronaphthalene (1.0 g, 3.56 mmol) was dissoved in methylvinylketone (dist., 0.468 g, 6.7 mmol) and this mixture was cooled down to 0° C. Triethylamine (3 drops) was then added and the mixture was stirred at 0° C. for an hour and then at room temperature overnight. The reaction mixture was dissolved in ethyl ether and concentrated to give the title material (1.09 g, 87%) as a yellow oil.

$^1$H NMR (CDCl$_3$, δ, ppm): 1.08 and 1.46 (2×3H, 2 s, 2×—CH$_3$), 1.86 (1H, d, J=14.2 Hz, H-6), 2.04–2.10 (2H, m, —CH$_2$—), 2.12 (3H, s, —COCH$_3$), 2.35–2.50 (2H, m, —CH$_2$CO—), 2.53 (1H, d, J=14.2 Hz, H-6), 7.27 (1H, d overlapped by CDCl$_3$, H-4), 7.66 (1H dd, J=8.4 and 2.3 Hz, H-3), 8.07 (1H, d, J=2.2 Hz, H-1), 9.82 (1H, s, —CHO).

EXAMPLE 3

6-Bromo-9,9-dimethyl-3-oxo-1,2,3,9,10,10a-hexahydrophenanthrene

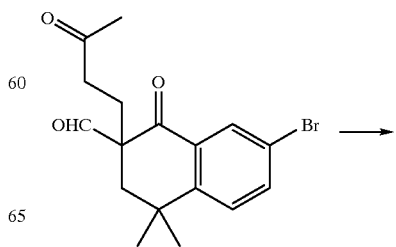

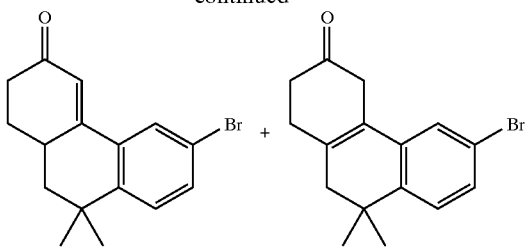

A solution of 7-bromo-4,4-dimethyl-2-formyl-2-(3-oxobutyl)-1-oxo-1,2,3,4-tetrahydronaphthalene (1.71 g, 4.87 mmol) in methanol (170 ml) was treated with a solution of lithium hydroxide hydrate (0.854 g, 20.35 mmol) in water (85 ml) the reaction was stirred at room temperature for 45 minutes and then the temperature was raised to 50° C. and the mixture was stirred for another 2 hours. The reaction was quenched with water and adjusted to pH 5 with 4M hydrochloric acid. The aqueous phases were extracted with ethylacetate (3×) and the combined organic phases were washed with water and dried over anhydrous magnesium sulfate. The residue was purified by silica gel chromatography (hexane/ethylacetate 95:5 to 90:10) to give the title material (0.631 g, 42%) along with 6-bromo-9,9-dimethyl-3-oxo-1,2,3,4,9,10-hexahydrophenanthrene (0.371 g, 25%).

$^1$H NMR (CDCl$_3$, δ, ppm): 1.25 and 1.35 (2×3H, 2 s, 2×—CH$_3$), 1.71–1.82 (2H, m, —CH$_2$—), 2.14–2.20 (1H, m, —CH$_2$—), 2.41–2.50 (1H, m, —CH$_2$—), 2.55–2.60 (1H, m, —CH$_2$—), 2.78–2.86 (1H, m, —CH$_2$—), 6.55 (1H, d, J=1.9 Hz, H-4), 7.30 (1H, d, J=8.5 Hz, H-8), 7.48 (1H, dd, J=8.5 and 2.0 Hz, H-7), 7.83 (1H, d, J=2.0 Hz, H-5).

EXAMPLE 4

6-Bromo-9,9-dimethyl-3-hydroxy-9,10-dihydrophenanthrene

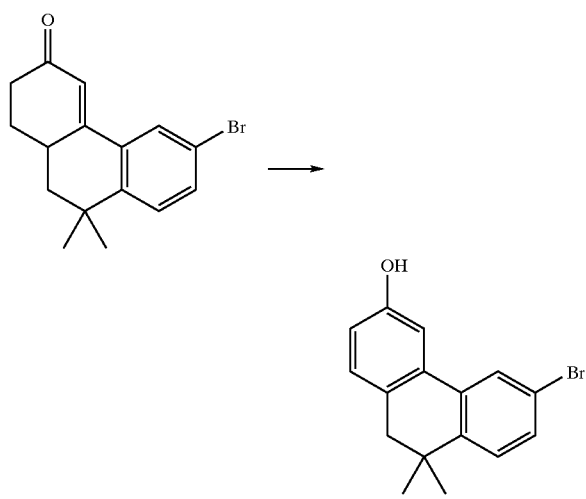

6-Bromo-9,9-dimethyl-3-oxo-1,2,3,9,10,10a-hexahydrophenanthrene (0.250 g, 0.819 mmol)), palladium (II) dichloride (0.190 g, 10.7 mmol) and tert-butanol (5 ml) were mixed in a sealed tube and heater to 125–135° C. for 4 hours. The reaction is finished when all the palladium has precipitated on the glass wall and a yellow and transparent reaction mixture is observed. Water was then added and the aqueous phase was extracted with ethyl acetate. The organic extracts were dried with anhydrous magnesium sulfate and concentrated. The residue was purified by silica gel chromatography (ethyl acetate/hexane 5:95 to 10:90) to give the title material (0.225 g, 91%).

$^1$H NMR (CDCl$_3$, δ, ppm): 1.22 (6H, s, 2×—CH$_3$), 2.68 (2H, s, —CH$_2$-10), 6.74 (1H, dd, J=8.1 and 2.5 Hz, H-7), 7.06 (1H d, J=8.1 Hz, H-8), 7.18 (1H d, J=2.5 Hz, H-5), 7.27 (1H, d overlapped by CDCl$_3$, H-1), 7.39 (1H, dd, J=8.2 and 2.0 Hz, H-2), 7.80 (1H, d, J=2.0 Hz, H-4).

EXAMPLE 5 a.) 4-(2-Tributylstannyl-vinyl)-benzoic acid, methyl ester

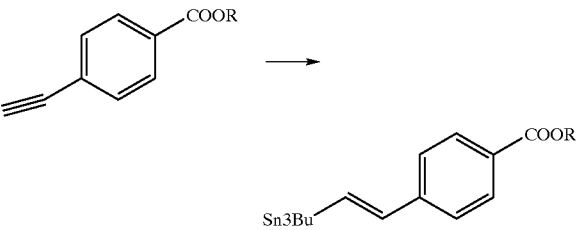

500 mg (3.1 mmol) 4-ethynyl-benzoic acid methyl ester, 1.3 ml (1.4 g; 4.8 mmol) tributyltin hydride and 50 mg (0.3 mmol) AIBN [1,1'-azobis(isobutyronitrile)] were dissolved in 5 ml benzene and refluxed for 2 hours. The reaction mixture was then cooled to room temperature, the solvent was removed under reduced pressure, and the residue was columned through silica using 1% Et$_3$N in 5% EtOAc/hexane to afford 1.35 g (96%) product as a light yellow oil.

$^1$H NMR (300 MHz, CDCl$_3$): 0.8–1.1 (m, 15H), 1.2–1.5 (m, 6H), 1.5–1.7 (m, 6H), 3.93 (s, 3H), 6.92 (d, 2H, 19.5 Hz), 7.08 (d, 2H, J=19.5 Hz), 7.48 (d, 2H, J=8.4 Hz), 8.00 (d, 2H, J=8.4 Hz); IR: cm$^{-1}$; MS (DCI): 451 (M+H)$^+$ b.) 4-(2-Tributylstannyl-vinyl)-benzoic acid, ethyl ester The title compound was prepared similarly to the methyl ester: A solution of ethyl 4-ethynylbenzoate (3.16 g, 18.1 mmol) in toluene (25 mL) was treated with 2,2'-azobisisobutyronitrile (AIBN) (0.300 g, 1.83 mmol) and tributyltin hydride (7.3 mL, 27.1 mmol). The mixture was heated to 90° C. for 1.5 hours. After cooling to room temperature, the solvent was evaporated and the residue was purified on silica gel (2% ethyl acetate/hexane+1% triethylamine) to give the title material (6.54 g, 78%) as a yellow oil.

c.) Ethyl 4-[2-(E)-[10,9-dihydro-9,9-dimethyl-3-hydroxy]-6-phenanthrenyl]ethenyl]benzoate

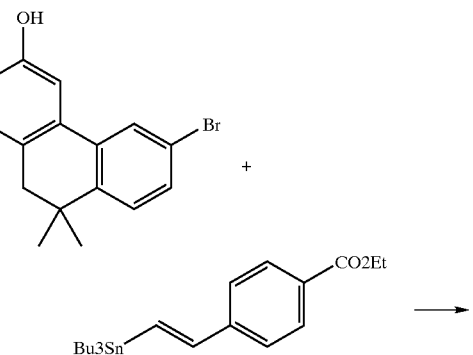

-continued

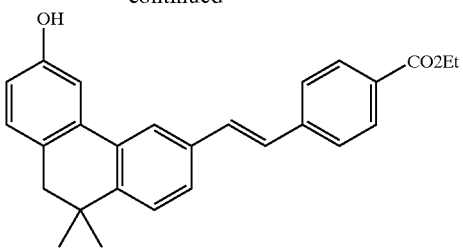

A solution of 6-bromo-9,9-dimethyl-3-hydroxy-9,10-dihydrophenanthrene (0.085 g, 0.28 mmol), ethyl 4-((2-tributylstannyl)ethenyl)benzoate (0.190 g, 0.408 mmol) and tetrakistriphenylphosphinepalladium(0) (28 mg) in toluene (5 ml) was heated to 100–105° C. for 6 hours. Water was added and the aqueous phase was extracted with ethyl acetate. The combined organic extracts were dried over anhydrous magnesium sulfate, filtered and concentrated. The residue was purified by silica gel chromatography (ethyl acetate/hexane 10:90 to 20:80) to give the title material.

$^1$H NMR (CDCl$_3$, δ, ppm): 1.26 (6H, s, 2×—CH$_3$), 1.41 (3H, t, J=7.1 Hz, —CH$_3$), 2.71 (2H, s, —CH$_2$-10), 4.40 (2H, qa, J=7.1 Hz, —OCH$_2$—), 6.76 (1H, dd, J=8.0 and 2.5 Hz, H-7'), 7.08 (1H, d, J=8.1 Hz, H-8'), 7.14 and 7.23 (2×1H, 2d, J$_{AB}$=16.3 Hz, vinyl H), 7.34 (1H, d, J=2.5 Hz, H-5'), 7.41 (1H, d, J=8.1 Hz, H-1'), 7.46 (1H, dd, J=8.1 Hz 1.3 Hz, H-2'), 7.57 (2H, d, J=8.2 Hz, H-3 and H-5), 7.84 (1H, br s, H-4'), 8.05 (2H, d, J=8.3 Hz, H-2 and H-6).

EXAMPLE 6

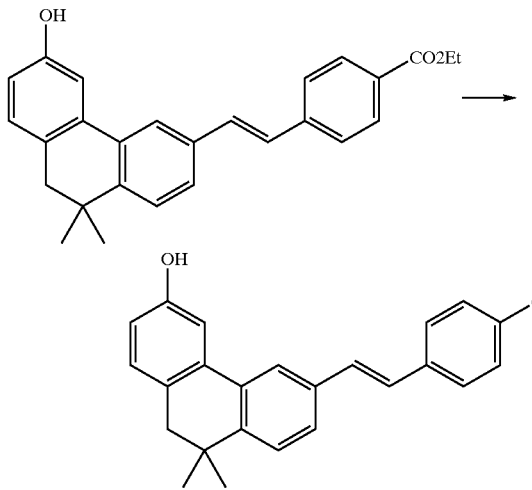

Ethyl 4-[2-(E)-[10,9-dihydro-9,9-dimethyl-3-methoxy]-6-phenanthrenyl]ethenyl]benzoate A solution of ethyl 4-[2-(E)-[10,9-dihydro-9,9-dimethyl-3-hydroxy]-6-phenanthrenyl]ethenyl]benzoate (0.074 g, 0.19 mmol) in acetone (5 ml) was treated with potassium carbonate (0.077 g, 0.56 mmol) and iodomethane (50 µl, 0.80 mmol). The mixture was heated under reflux for 3 hours and treated again with potassium carbonate (0.090 g, 0.65 mmol) and iodomethane (500 µl, 8.0 mmol). The mixture was heated again under reflux for 5 additional hours in adding enough iodomethane to complete the reaction. The mixture was cooled down to room temperature and filtered and the solvent was evaporated. The residue (0.151 g) was purified on TLC plates (15% ethyl acetate/hexane) and gave the title material (0.045 g, 57%). $^1$H NMR (DMSO-d$_6$, δ, ppm): 8.12 (1H, s, H-4), 7.98 (2H, d, J=8.8 Hz, H-2 and H-6), 7.77 (2H, d, J=8.8 Hz, H-3 and H-5), 7.60 (1H, dd, J=8.1 Hz, H-2'), 7.52–7.45 (4H, m, H-5', H-1' and vinyl H), 7.18 (1H, d, J=8.8 Hz, H-8'), 6.87 (1H, dd, H-7'), 4.33 (2H, qa, J=7.3 Hz, —CH$_2$O—), 3.85 (3H, s, —OMe), 2.69 (2H, s, —CH$_2$-10), 1.34 (3H, t, J=7.3 Hz, —CH$_3$), 1.20 (6H, s, 2×—CH$_3$). MS (ESI): 413.10 (M+H)$^+$

EXAMPLE 7

4-[2-(E)-[10,9-Dihydro-9,9-dimethyl-3-methoxy]-6-phenanthrenyl]ethenyl]benzoic acid

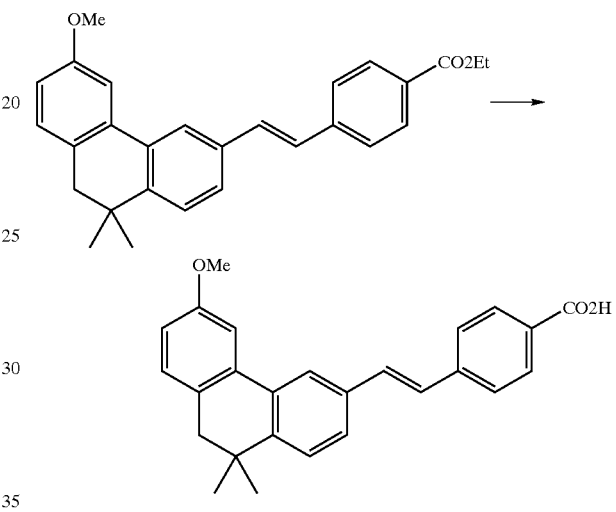

A solution of ethyl 4-[2-(E)-[10,9-dihydro-9,9-dimethyl-3-methoxy]-6-phenanthrenyl]ethenyl]benzoate (0.037 g, 0.090 mmol) was degassed with argon and then treated with NaOH (5N, 70 µl, 0.35 mmol). The mixture was stirred at room temperature for 20 hours. NaOH (5N, 100 µl, 0.5 mmol) was added again and the reaction was stirred for 6 additional hours. The mixture was diluted with ethyl acetate (25 ml) and poured into a solution of 1N HCl (20 ml). The organic phases were separated and the aqueous phase was extracted with ethylacetate (2×5 ml). The combined organic extracts were washed with water and brine, dried over anhydrous magnesium sulfate, filtered and concentrated. The residue was dissolved into a mixture of ethyl ether/dichloromethane and hexane was added. The solution was concentrated under vacuum and the solid was filtered. The solid was dissolved in methanol, ethanol and ethyl ether. The solution was filtered on a fiber glass paper and evaporated. Water was added to the residue and the product was lyophilized to give the title material (compound 10) as a white solid.

$^1$H NMR (DMSO-d$_6$, δ, ppm): 8.12 (1H, s, H-4'), 7.98 (2H, d, J=8.8 Hz, H-2 and H-6), 7.77 (2H, d, J=8.8 Hz, H-3 and H-5), 7.60 (1H, dd, J=8.1 Hz, H-2'), 7.52 (1H, d, H-5'), 7.47 (2H, s, vinyl H), 7.46 (1H, d, J=8.1 Hz, H-1'), 7.18 (1H, d, J=8.1 Hz, H-8'), 6.87 (1H, dd, J=8.1 and 2.1 Hz, H-7'), 3.85 (3H, s, —OMe), 2.69 (2H, s, —CH$_2$-10), 1.20 (6H, s, 2×—CH$_3$). MS (ESI): 383.07 (M–H)$^-$. HRMS for C$_{26}$H$_{23}$O$_3$ Calcd: 383.16473 Found: 383.16320

EXAMPLE 8

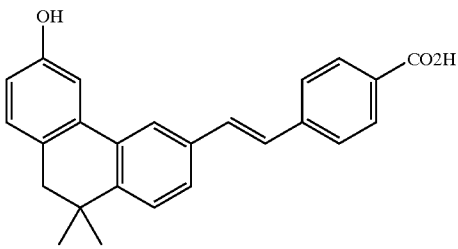

4-[2-(E)-[10,9-Dihydro-9,9-dimethyl-3-hydroxy]-6-phenanthrenyl]ethenyl]benzoic acid A solution of ethyl 4-[2-(E)-[10,9-dihydro-9,9-dimethyl-3-hydroxy]-6-phenanthrenyl]ethenyl]benzoate (0.040 g, 0.10 mmol) in tetrahydrofuran (1.5 ml) and ethanol (1.5 ml) was treated with an aqueous solution of sodium hydroxide (5M, 0.142 ml, 0.71 mmol) and the reaction was stirred overnight. The reaction was then diluted with water (~10 ml) and acidified by the addition of aqueous HCl (4M). The precipitated product was filtered and washed with water. The residual solid was purified by Prep HPLC and afforded the title material (compound 8) (18 mgs, 49%) as a white fluffy solid.

$^1$H NMR (DMSO-d$_6$, δ, ppm): 1.20 (6H, s, 2x—CH$_3$), 2.64 (2H, s, —CH$_2$-10'), 6.71 (1H, d, J=8.0 Hz, H-1' or H-8'), 7.05 (1H, d, J=8.1 Hz, H-1' or H-8'), 7.34(1H,s,H-5'), 7.40–7.51 (3H, m, vinyl H and H-7'), 7.58 (1H, d, J=8.0 Hz, H-2'), 7.75 (2H, d, J=8.0 Hz, H-3 and H-5), 7.94 (1H, s, H-4'), 7.97 (2H, d, J=8.0 Hz, H-2 and H-6), 9.29 (1H, s, —OH), 12.89 (1H, s, —CO$_2$H).

IR ν (cm$^{-1}$): 3401, 3188, 2961, 1685 (C=O) and 1602.

EXAMPLE 9

Assay methodology (retinoic acid is used as a positive control in all assays):

Competition Binding Assay Using Yttrium SPA Beads

Principle of the assay: The Yttrium SPA beads have the property of binding to the His-tag-fused Ligand Binding Domain (LBD) of RARα, β and γ iso-types. The binding of a tritiated RAR-ligand ([$^3$H]-tRA) to the RAR LBD will stimulate the SPA bead creating an emission of fluorescence measured in a scintillation top count counter.

Protocol: His-RARα, β or γ were over-expressed in *E. coli* BL21 (DE3) strain according to the protocol described by Rochel et al. (Rochel et al., 1997, Biochem. Biophys. Res. Com. 230, 293–297). The competition binding assay was performed in 96 well opti-plates (Packard) in Tris-HCl 20 mM pH 8, NaCl 100 mM, BSA 0.5% and in a final volume of 80 μl. In this order was added, 10 μl of His-RARα, β or γ (the quantity of protein added in the assay was primarily defined by titration), 50 μl of 8 times diluted Ytrium SPA beads, 10 μl of increasing concentrations of competitor ranging from 0.1 nM to 10 μM and 10 μl of a saturating concentration (5 nM) of [3H]-all trans Retinoic Acid (NEN life Sciences). The non-specific binding of the radioligand was determined in the presence of 500-fold excess of cold all-trans Retinoic Acid. The plates were incubated 2h at 4° C. under gentle shaking and counted in a top count scintillation counter (Packard). Binding data are reported as apparent Kd's, in nM Transactivation Assay The transactivation assay measures the ability of a retinoid to activate a reporter gene in the presence of one of the retinoic acid receptor subtypes (.alpha., .beta., or gamma.). Activation of just one receptor and failure to activate another is the basis for selectivity/specificity. In our definitions, "selectivity" means that the compound preferentially activates one receptor but also activates at least one other at a higher concentration and "specificity" means that the compound activates only one receptor in the concentration range tested. The details of the receptor-based transactivation assay are disclosed in the literature, e.g. see Nature 1988, 332, 85C-853.

Principle of the assay: The agonistic, antagonistic or mixed agonist/antagonist activity of the compound was determined in stable HeLa cell lines which are expressing the chimerical receptors, GAL-RARα, β or γ along with the (17 mer)x5-Glob-Luc reporter gene. The chimerical receptors GAL-RARs were the result of the fusion between the DNA Binding Domain of the yeast transcription factor GAL4 and the LBDs of RARα, β or γ. The reporter gene contains the Luciferase coding sequence downstream to the minimal promoter of the Globine gene, all together under the control of 5 repeats of the GAL4 DBD response element, 17 mer. The culture of the cells in the presence of increasing concentration of compound ranging from 1 pM to 1 μM will define the agonistic potential of the ligand. Inversely, incubation of the cells with a saturating concentration of all trans Retinoic (10 nM) giving 100% of activation and in the presence of the same range of the compound concentrations (1 pM to 1 μM) will characterize any antagonistic potential of the retinoid.

Protocol: 1.5×10$^4$ cells are plated per well of 96 well plates and let adhering overnight to the support. The next day, the ligands are added and incubated for 24 hours. The expression of the Luciferase is measured by using the "Luc Lite" kit from Packard according to the recommendations of the manufacturer. Transactivation data are reported as EC$_{50}$'s in nM Growth Assay Principle of the assay: The proliferation of the cells was measured by the incorporation of [$^3$H]-Thymidine in the DNA of dividing cells.

Protocol: The number of cells which was plated has been primarily defined to avoid the cells reaching confluence before the end of the experiment duration (T47D & HT3, 750 cells/well; H3396, 200 cells/well of 96 well plates). The first day, the cells were plated in 96 well plates and incubated overnight at 37° C. (in O$_2$, 95%; CO$_2$, 5%), allowing the cells adhering to the support. The next day, the compounds were added to the cells and incubated for 3 or 6 days (note: for the 6-day incubation, the medium was replaced at Day3). At the end of the treatment, 10 μl of [$^3$H]-thymidine (final concentration of 0.4 μCi/well) were added for 4 hours at 37° C., the medium was finally removed, the cells trypsinized and harvested under vacuum on GF/B glass fiber filters. After 3 washes with distilled water, the filter were dried and counted in a scintillation counter after adding 50 μl of Microscint (Packard) to each filter. The percentage of growth inhibition was calculated by using DMSO as reference, which is the vehicle of the compounds. Growth inhibition is reported as IC$_{50}$'s in nM The structures and data for compounds 8 and 10 are shown below:

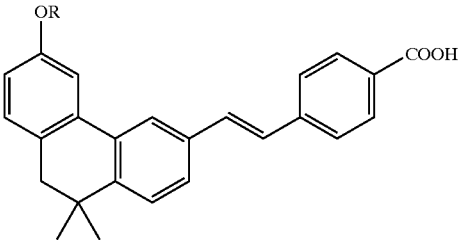

Compound 8, R = H
Compound 10, R = CH₃

| Compound | Binding (Kd, nM) | | | Transactivation (EC$_{50}$, nM) | | | Cell Growth Inhibition (IC$_{50}$, nM) | |
|---|---|---|---|---|---|---|---|---|
| | RARα | RARβ | RARγ | RARα | RARβ | RARγ | T47D | HT3 |
| 8 | 8.3 | 18.6 | 52.8 | 13.5 | 1.76 | 47 | 4.8 | 1161 |
| 10 | 1.1 | 1.6 | 10.6 | 0.02 | 0.005 | 1.9 | <0.01 | <0.01 |
| Retinoic acid | 2.4 | 1.6 | 1.0 | 0.4 | 0.08 | 0.1 | 6.5 | 1 |

As can be seen from the table above, compounds 8 and 10 are both active in all three assay systems, with compound 10 being the more active. Its binding and transactivation properties compare very favorably with those of the highly active natural ligand, retinoic acid, being essentially the same for the RARα and RARβ receptor, with some decrease in activity at the RARγ receptor. However, it has significantly enhanced inhibition against the two tested cell lines. Without wishing to be bound by any particular theory, it is believed that compounds 8 and 10 may be more stable metabolically than the relatively labile retinoic acid, and that their greater persistence is the cause of their greater activity.

We claim:

1. A compound represented by formula I

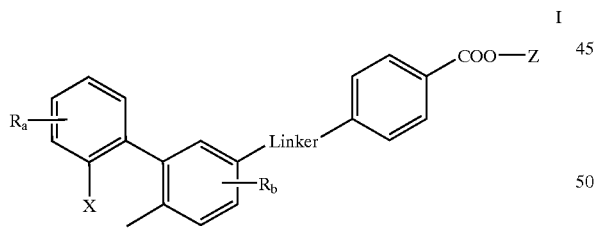

I or a nontoxic phamaceutically acceptable salt, physiologically hydrolyzable ester or solvate thereof, wherein R$_a$ and R$_b$ are independently selected from the group consisting of hydrogen, halogen, hydroxy, nitro, amino, substituted amino, mercapto, polyfluoroalkyl, C$_{1-6}$ alkyl, substituted C$_{1-6}$ alkyl, C$_{1-6}$ alkoxy, C$_{1-6}$ alkylthio, formyl, carboxyl, aryl or heteroaryl;

Linker is selected from the group consisting of C$_2$ alkyl, C$_2$ alkenyl, C$_2$ alkynyl, —C(=O)—NH—, —NH—C(=O)—, —CH$_2$O—, —O—C(=O)—, —C(=S)—NH—, —(=O)—O—, —C(=O)—S—, —S—C(=O)—, —S—CH$_2$—, —CH$_2$—NH—, —C(=O)—CH$_2$—, —NH—C(=S)—, —CH$_2$S—, —OCH$_2$—, —NHCH$_2$;

X is O, S, —(R$_1$)$_2$, C=O, —C(R$_1$)$_2$Y— or —YC(R$_1$)$_2$—, wherein Y is selected from the group consisting of O, S and C(R$_2$)$_2$, wherein R$_1$ and R$_2$ are, independently, hydrogen or methyl; and Z is hydrogen or C$_{1-6}$ alkyl.

2. A compound represented by formula I

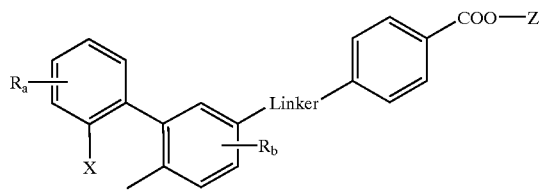

or a nontoxic pharmaceutically acceptable salt, physiologically hydrolyzable ester or solvate thereof, wherein R$_a$ and R$_b$ are independently selected from the group consisting of hydrogen, halogen, hydroxy, nitro, amino, mercapto, CF$_3$, C$_{1-6}$ alkyl, halosubstituted C$_{1-6}$ alkyl, hydroxy-substituted C$_{1-6}$ alkyl, aminosubstituted C$_{1-6}$ alkyl, C$_{1-6}$ alkoxy, C$_{1-6}$ alkyithio, formyl, carboxyl, mono- or di-C$_{1-6}$ alkyl-substituted amino, aryl or heteroaryl;

Linker is selected from the group consisting of —CH=CH—, —C≡C—, —C(=O)—NH—, —NH—C(=O)—, —CH$_2$O—, —O—C(=O)—, —C(=S)—NH—, —C(=O)—O—, —C(=O)—S—, —S—C(=O)—, —S—CH$_2$—, —CH$_2$—CH$_2$—, —CH$_2$—NH—, —C(=O)—CH$_2$—, —NH—C(=S)—, —CH$_2$S—, —OCH$_2$—, —NHCH$_2$ or —CRc=CRd—, wherein Rc and Rd are independently hydrogen or C$_{1-6}$ alkyl;

X is O, S, —C(R$_1$)$_2$, C=O, —C(R$_1$)$_2$Y— or —YC(R$_1$)$_2$—, wherein Y is selected from the group consisting of O, S and $C(R_2)_2$, and $R_1$ and $R_2$ are, independently, hydrogen or methyl; and Z is hydrogen or $C_{1-6}$ alkyl.

3. The compound of claim 2 wherein X is —$C(R_1)_2Y$— or —$YC(R_1)_2$—, wherein Y is selected from the group consisting of O, S and $C(R_2)_2$ and $R_1$ and $R_2$ are, independently, hydrogen or methyl.

4. The compound of claim 3 wherein Linker is —CH=CH— or —C≡C—.

5. A pharmaceutical composition comprising a therapeutically effective amount of a compound of claim 1 and a pharmaceutically acceptable carrier therefor.

6. A pharmaceutical composition comprising a therapeutically effective amount of a compound of claim 2 and a pharmaceutically acceptable carrier therefor.

7. A pharmaceutical composition comprising a therapeutically effective amount of a compound of claim 3 and a pharmaceutically acceptable carrier therefor.

* * * * *

UNITED STATES PATENT AND TRADEMARK OFFICE
CERTIFICATE OF CORRECTION

PATENT NO.    : 6,825,233 B2
DATED         : November 30, 2004
INVENTOR(S)   : Ericsson et al.

It is certified that error appears in the above-identified patent and that said Letters Patent is hereby corrected as shown below:

Column 35,
The second structure in Example 6, should be

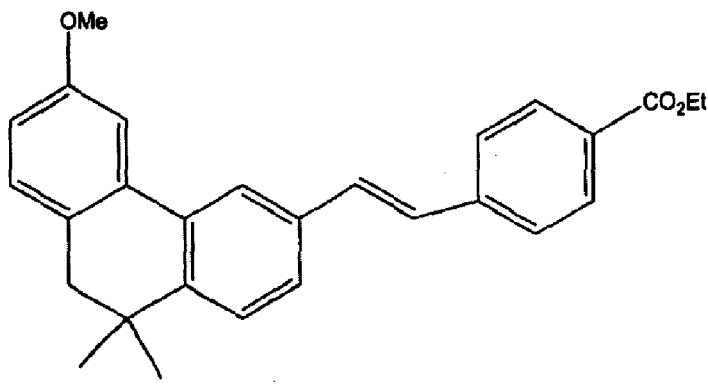

Column 37,
Line 46, the "Protocol" should read -- His-RARα, β or γ"

Column 39,
Line 64, the "Linker" should be defined as -- –C(=O)-O- --, rather than -- –(=O)-O- --.

Signed and Sealed this

Tenth Day of May, 2005

JON W. DUDAS
*Director of the United States Patent and Trademark Office*